United States Patent
Lagrange

(10) Patent No.: US 7,611,546 B2
(45) Date of Patent: Nov. 3, 2009

(54) COMPOSITION COMPRISING AT LEAST ONE SUBSTITUTED ACETYLENIC CARBOCYANIN DERIVATIVE, PROCESS FOR TREATING KERATIN FIBRES USING IT, AND DEVICE THEREFOR

(75) Inventor: Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/081,310

(22) Filed: Apr. 14, 2008

(65) Prior Publication Data

US 2009/0064423 A1    Mar. 12, 2009

Related U.S. Application Data

(60) Provisional application No. 60/924,036, filed on Apr. 27, 2007.

(30) Foreign Application Priority Data

Apr. 13, 2007  (FR) .................... 07 54453

(51) Int. Cl.
*A61Q 5/10* (2006.01)
(52) U.S. Cl. .................. 8/405; 8/426; 8/435; 8/565
(58) Field of Classification Search ............. 8/405, 8/426, 435, 565
See application file for complete search history.

(56) References Cited

U.S. PATENT DOCUMENTS 3,414,568 A    12/1968   Collet et al.
2002/0132797 A1*  9/2002   Kerwin et al. ............... 514/151
2006/0021161 A1*  2/2006   Lagrange et al. ............... 8/405

FOREIGN PATENT DOCUMENTS

WO    WO 00/03709    1/2000
WO    WO 2006/087194    8/2006

OTHER PUBLICATIONS

STIC Search Report dated Feb. 20, 2009.*
French Search Report for French Application No. 0754453 dated Nov. 21, 2007.
European Search Report for European Application No. 08 15 4421 dated Oct. 13, 2008.

* cited by examiner

*Primary Examiner*—Eisa B Elhilo
(74) *Attorney, Agent, or Firm*—Finnegan Henderson Farabow Garrett & Dunner L.L.P.

(57) ABSTRACT

The invention relates to a composition for dyeing human keratin fibers, comprising, in a cosmetically acceptable medium, one or more cationic direct dyes comprising at least one carbon-carbon triple bond, for instance dyes of formula (I), (II) or (III) below:

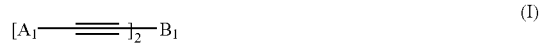
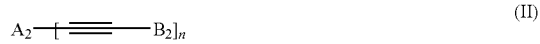
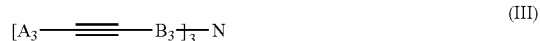

in which $A_1$, $A_2$ and $A_3$, independently of each other, correspond to a cationic heterocyclic group and $B_1$, $B_2$ and $B_3$, independently of each other, correspond to a particular aromatic nucleus; n may be equal to 1 or 2.

15 Claims, No Drawings

COMPOSITION COMPRISING AT LEAST ONE SUBSTITUTED ACETYLENIC CARBOCYANIN DERIVATIVE, PROCESS FOR TREATING KERATIN FIBRES USING IT, AND DEVICE THEREFOR

CROSS-REFERENCE TO RELATED APPLICATIONS

This application claims benefit of priority under 35 U.S.C. §119 to French Patent Application No. 0754453, filed Apr. 13, 2007, and the benefit of U.S. Provisional Application No. 60/924,036, filed Apr. 27, 2007, the content of all of which is incorporated herein by reference.

The invention relates to a composition comprising, in a cosmetically acceptable medium, at least one cationic direct dye of the carbocyanin family bearing an acetylenic bond (carbon-carbon triple bond).

The invention also concerns a process for treating keratin fibres using such a composition, and a device comprising it.

The present invention relates to the field of dyeing keratin fibres and more particularly the dyeing of human keratin fibres such as the hair.

Many compositions and many processes exist for dyeing keratin fibres, and in particular human hair.

Thus, it is known practice to dye keratin fibres, and in particular human hair, with dye compositions containing oxidation dye precursors, in particular ortho- or para-phenylenediamines, ortho-aminophenols or para-aminophenols and heterocyclic compounds such as diaminopyrazole derivatives, which are generally referred to as oxidation bases. Oxidation dye precursors, or oxidation bases, are colourless or weakly coloured compounds which, when combined with oxidizing products, give rise to coloured compounds and dyes via a process of oxidative condensation.

It is also known that the shades obtained with these oxidation bases can be varied by combining them with couplers or colouration modifiers, the latter being chosen in particular from aromatic meta-diamines, meta-aminophenols, meta-diphenols and certain heterocyclic compounds.

The variety of molecules used as oxidation bases, on the one hand, and as couplers, on the other hand, allows a wide range of colours to be obtained.

The "permanent" colouration obtained by means of these oxidation dyes must moreover satisfy a certain number of requirements. Thus, it must have no toxicological drawbacks and it must allow shades of the desired strength to be obtained and have good resistance to external agents such as light, bad weather, washing, permanent waving, perspiration and rubbing.

The dyes must also allow grey hair to be covered, and, lastly, they must be as unselective as possible, i.e. they must allow the smallest possible differences in colouration to be produced over the entire length of the same keratin fibre, which may indeed be differently sensitized, i.e. damaged, between its tip and its root.

It turns out, in conclusion, that although standard base-coupler combinations afford a wide range of colours, they do not satisfy the criteria listed above, and, especially, often lead to the generation in the fibre of varied coupling products, giving rise to fastness problems that are difficult to master, for instance a selective colour change.

Moreover, the permanent colouration with oxidation dyes usually requires the use of oxidizing systems that might harm the integrity of the keratin fibres (sensitization of the hair).

Another way of dyeing keratin fibres, in particular the hair, is to use direct dyes.

The standard dyes that are used are, in particular, dyes of the nitrobenzene, anthraquinone, nitropyridine, azo, cationic azo, xanthene, acridine, azine or triarylmethane type, or natural dyes.

These dyes, which are coloured and colouring molecules that have an affinity for fibres, are applied to the keratin fibres for the time required to obtain the desired colouration, and are then rinsed out.

As a result, direct dyeing is very widely practiced since it also offers certain advantages over oxidation dye precursors, and especially, often, better harmlessness and an absence of sensitization of the hair due to the oxidative process.

The colourations obtained are, however, temporary or semi-permanent, since the nature of the interactions that bind the direct dyes to the keratin fibre, and their desorption from the surface and/or the core of the fibre, are responsible for their relatively poor dyeing power and fastness with respect to washing, bad weather or perspiration. These direct dyes are also generally light sensitive due to the poor resistance of the chromophore with respect to photochemical attack, and lead over time to fading of the colouration of the hair.

The kinetics of absorption of these direct dyes by keratin fibres are moreover not fast enough to obtain intense colourations with short leave-in times.

There is thus a need for a composition for dyeing keratin fibres, in particular human keratin fibres and more particularly the hair, which shows good harmlessness with respect to the keratin fibres, which is sparingly selective, which gives a wide variety of strong colours, and which also makes it possible to obtain a fast, stable colouration on keratin fibres that is resistant to external agents, such as light, bad weather, washing, perspiration, rubbing and subsequent treatments, such as permanent waving, and which may be rapid enough to allow, where necessary, the use of short leave-in times.

There is still a need for a dye composition that allows the treatment of all kinds of keratin fibres, and of all types of hair, for example grey hair, even if this hair has undergone a treatment beforehand, such as a bleaching or permanent-waving treatment.

Finally, there is a need for a composition that performs dyeing without it being necessary to sensitize the keratin fibre or the hair beforehand.

The aim of the present invention is to provide a composition for dyeing keratin fibres, in particular human keratin fibres and more particularly the hair, which satisfies, inter alia, the needs listed above.

The aim of the present invention is also to provide a composition for dyeing keratin fibres that does not have the drawbacks, defects, limitations and disadvantages of the dye compositions of the prior art, whether they are dye compositions using a base-coupler combination, or compositions using a direct dye.

This aim and others are achieved, in accordance with the invention, by means of a composition for dyeing keratin fibres, comprising, in a cosmetic medium that is suitable for dyeing, at least one cationic direct dye comprising at least one carbon-carbon triple bond $$(-\!\!\equiv\!\!-).$$

A subject of the invention is also a process for treating keratin fibres, more particularly human keratin fibres, in which the composition according to the invention is applied to the said wet or dry fibres.

Another subject of the invention consists of a multi-compartment device, at least one compartment of which comprises the composition according to the invention and at least one other compartment comprises an oxidizing agent.

However, other characteristics and advantages of the invention will emerge more clearly on reading the description and the examples that follow.

In the text hereinbelow, and unless otherwise mentioned, the limits of a range of values are considered as forming part of that range.

According to the present invention, the term "human keratin fibres" means the hair, the eyelashes and the eyebrows.

It should be noted that the composition is suitable for treating human keratin fibres, irrespective of their colouration before treatment and whether or not this treatment is natural or obtained artificially.

As indicated previously, the composition according to the invention comprises at least one cationic direct dye comprising at least one carbon-carbon triple bond.

In accordance with one particular variant, the dye composition comprises, in a cosmetically acceptable medium, one or more direct dyes of formula (I), (II) or (III) below:

  (I)

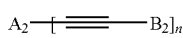  (II)

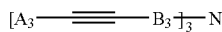  (III)

in which formulae:
  $A_1$, $A_2$ and $A_3$, independently of each other, correspond to a cationic heterocyclic group preferably chosen from pyridinium, (benz)imidazolium, (benzo)thiazolium, benzoxazolium, (iso)quinolinium, (benz)indolium, acridinium, thioxanthilium, quinolizinium, phenazinium and pyrrolopyridinium groups, attached to the C≡C functions) via one of the carbon atoms of the heterocycle or of the aromatic nucleus to which the heterocycle is optionally fused;
  $A_1$, $A_2$ and $A_3$ may be optionally substituted, beyond the radicals borne by the quaternized nitrogen atoms, with one or more identical or different radicals chosen from halogen atoms, for instance fluorine or chlorine, $C_1$-$C_{25}$ alkyl radicals, ($C_1$-$C_4$) alkoxy radicals, ($C_1$-$C_{20}$)alkylcarbonylamino radicals and phenyl radicals;
  the quaternized nitrogen atom(s) of the heterocycle, when it is (they are) present, optionally bear(s) an amino radical; a $C_2$-$C_{20}$ acyl radical; a $C_1$-$C_{25}$ alkyl radical optionally substituted with at least one phenyl, phenyl-carbonyl, ($C_1$-$C_4$)alkoxycarbonyl, sulfo (—$SO_3M$ with M representing a hydrogen atom or an alkali metal), ethylenyl (—CH=$CH_2$), acetylenyl (—C≡CH) or phenyl-acetylenyl (—C≡C—$C_6H_5$) radical;
  $B_1$, $B_2$ and $B_3$, independently of each other, correspond to an aromatic nucleus chosen from phenyl, anthracenyl and naphthyl groups, attached to one or two C≡C functions;
  $B_1$, $B_2$ and $B_3$ may be optionally substituted with one or more amino groups optionally bearing one or two identical or different radicals chosen from $C_1$-$C_{18}$ alkyl, ($C_1$-$C_{20}$)alkylcarbonyl, ($C_1$-$C_{20}$)alkylsulfonyl and phenyl optionally substituted with a $C_1$-$C_4$ alkoxy group; hydroxyl; $C_1$-$C_4$ alkoxy; $C_1$-$C_{10}$ alkyl optionally bearing an amino group; phenoxy; sulfo (—$SO_3M$ with M representing a hydrogen atom or an alkali metal); cyano; trifluoromethyl; halogen chosen from chlorine, fluorine and bromine; acetylthio ($CH_3$—CO—S—);
  n is equal to 1 or 2;
  the electrical neutrality of the compounds being assured, if necessary, by means of one or more identical or different cosmetically acceptable anions.

According to a first particular embodiment of the invention, the direct dye is of formula (I) and the group $A_1$ is a phenazinium group.

According to this embodiment, the group $B_1$ is preferably an anthracenyl group.

According to a second embodiment of the invention, the direct dye is of formula (II).

In a first variant, n is 1 and the group $A_2$ is preferably chosen from optionally substituted pyridinium, benzimidazolium, (benzo)thiazolium, benzoxazolium, (iso)quinolinium, (benz)indolium, acridinium, thioxanthilium, quinolizinium and pyrrolopyridinium groups.

In a second variant, n is 2 and the group $A_2$ is preferably a pyridinium group.

Irrespective of the variant selected, the groups $B_2$, independently of each other, correspond to an optionally substituted phenyl or a naphthyl group. Preferably, the groups $B_2$ are identical.

According to a third embodiment of the invention, the direct dye is of formula (III) and the groups $A_3$ are pyridinium groups.

In accordance with this embodiment, the groups $B_3$ are preferably phenyl groups. Preferably, the groups $B_2$ are identical.

In formula (I), (II) or (III), the cosmetically acceptable anions(s) is (are) more particularly chosen from halides, sulfates, bisulfates, nitrates, phosphates, hydrogen phosphates, dihydrogen phosphates, carbonates, bicarbonates, perchlorates, salts of mono- or polycarboxylic or sulfonic acids, which may be saturated or unsaturated, and aromatic or non-aromatic, optionally substituted with at least one hydroxyl or amino radical, or at least one halogen atom; phenols.

In accordance with one particularly advantageous embodiment of the invention, the direct compound corresponds to one of the following formulae:

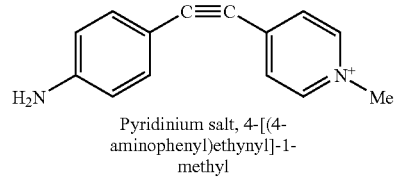

Pyridinium salt, 4-[(4-aminophenyl)ethynyl]-1-methyl

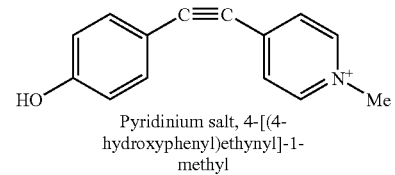

Pyridinium salt, 4-[(4-hydroxyphenyl)ethynyl]-1-methyl

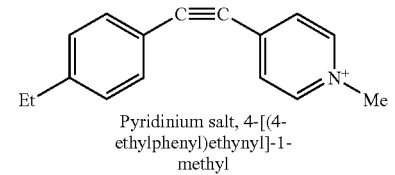

Pyridinium salt, 4-[(4-ethylphenyl)ethynyl]-1-methyl

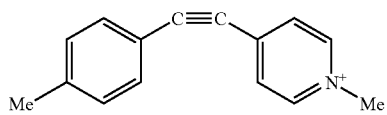

Pyridinium salt, 1-methyl-4-[(4-methylphenyl)ethynyl]

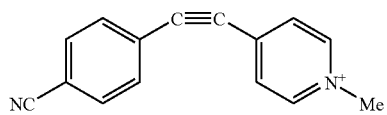

Pyridinium salt, 4-[(4-cyanophenyl)ethynyl]-1-methyl

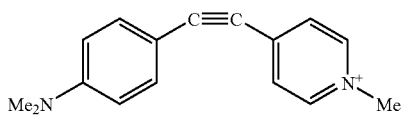

Pyridinium salt, 4-[[4-(dimethylamino)phenyl]ethynyl]-1-methyl

Salt of 4-methylbenzenesulfonic acid (1:1) and of pyridinium, 4-[[4-(dimethylamino)phenyl]-ethynyl]-1-methyl-, monohydrate

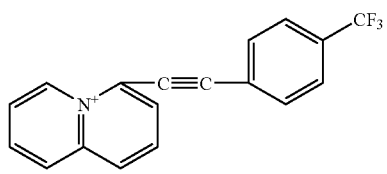

Quinolizinium salt, 4-[[4-(trifluoromethyl)phenyl]-ethynyl]-

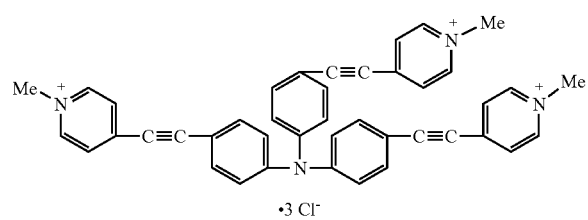

Pyridinium trichloride, 4,4',4''-[nitrilotris(4,1-phenylene-2,1-ethynediyl)]tris[1-methyl-,trichloride

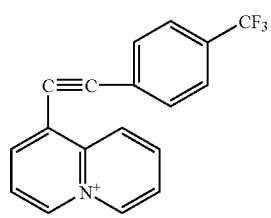

Quinolizinium salt, 1-[[4-(trifluoromethyl) phenyl]-ethynyl]-

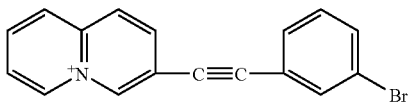

Quinolizinium salt, 3-[(3-bromophenyl)ethynyl]-

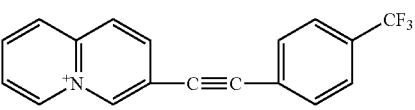

Quinolizinium salt, 3-[[4-(trifluoromethyl)phenyl]-ethynyl]-

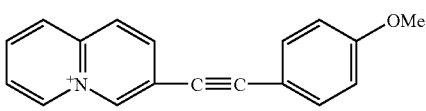

Quinolizinium salt, 3-[(4-methoxyphenyl)ethynyl]-

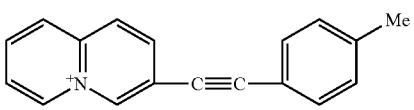

Quinolizinium salt, 3-[(4-methylphenyl)ethynyl]-

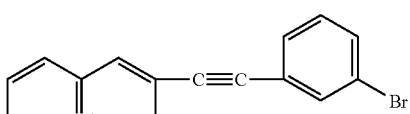

Quinolizinium salt, 2-[(3-bromophenyl)ethynyl]-

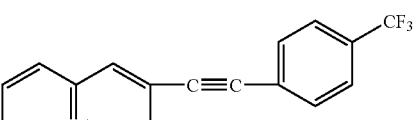

Quinolizinium salt, 2-[[4-(trifluoromethyl)phenyl]-ethynyl]

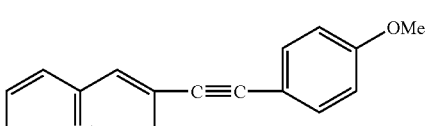

Quinolizinium salt, 2-[(4-methoxyphenyl)ethynyl]

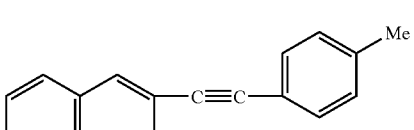

Quinolizinium salt, 2-[(4-methylphenyl)ethynyl]-

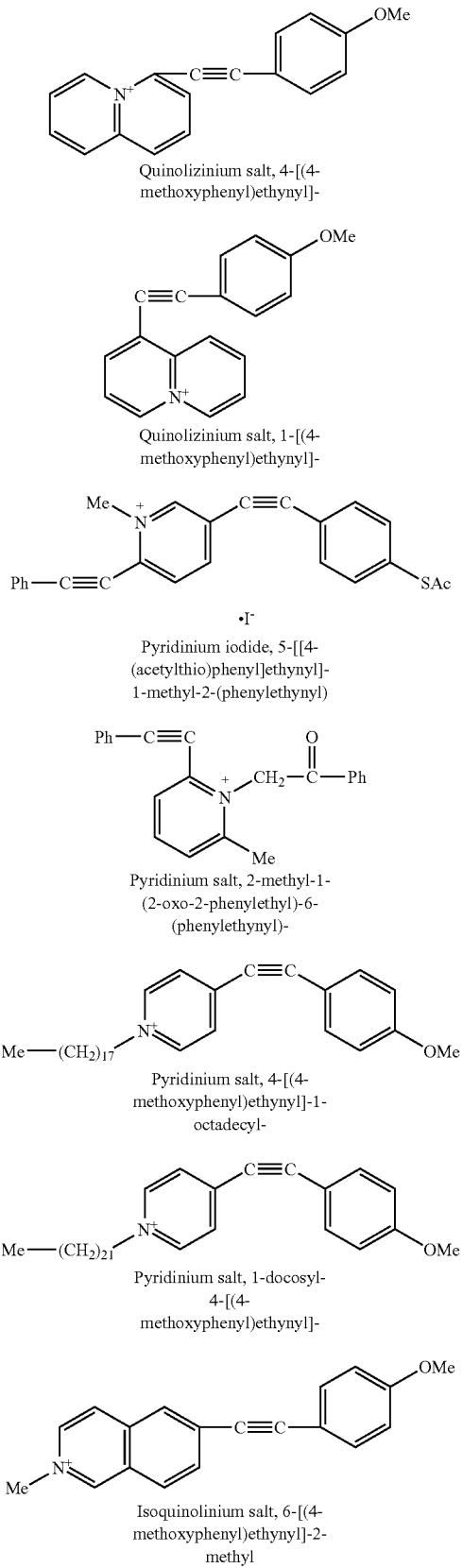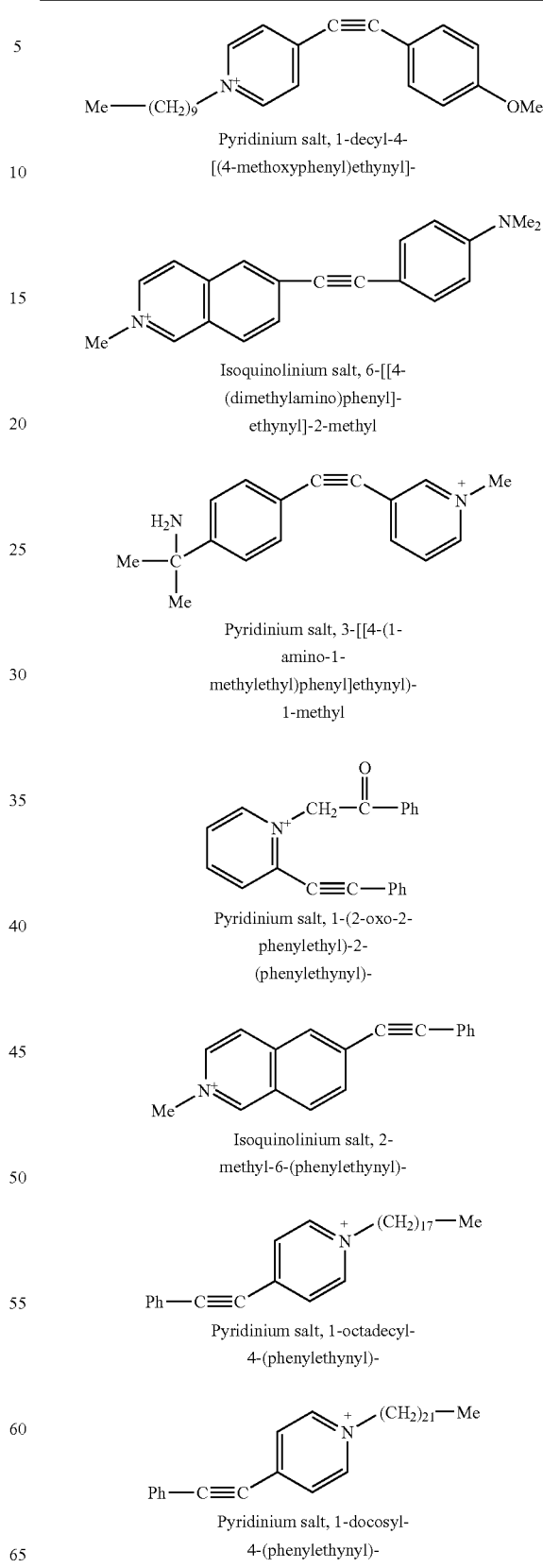

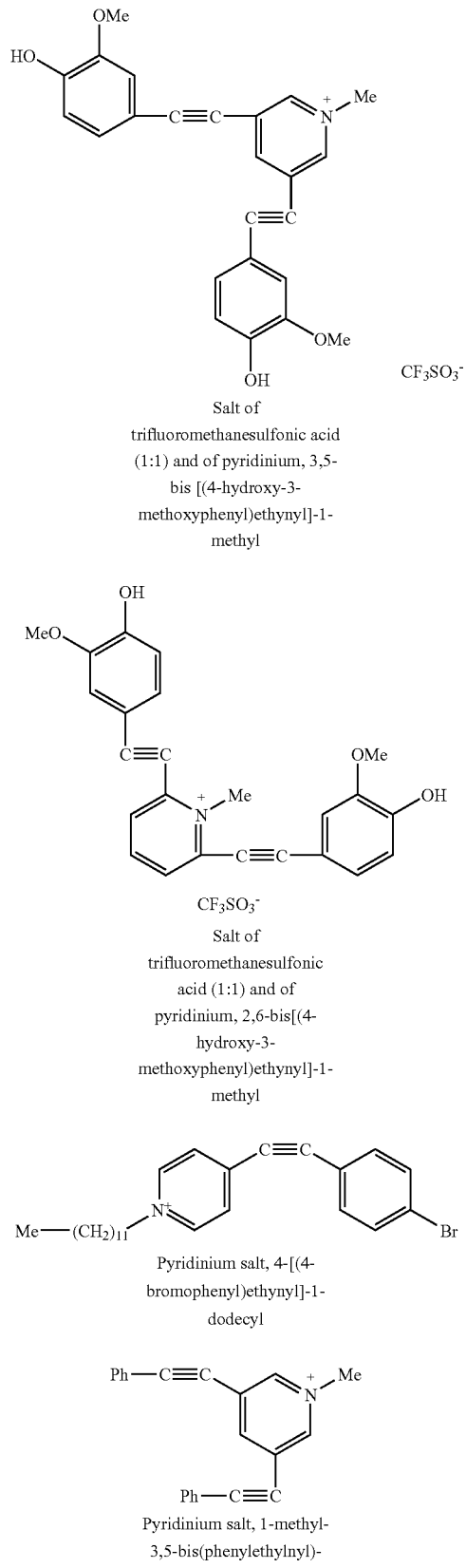

-continued

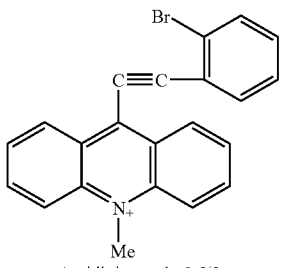

Acridinium salt, 9-[(2-bromophenyl)ethynyl]-10-methyl

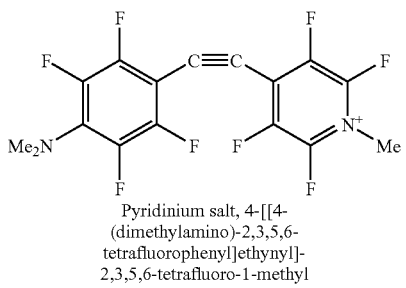

Pyridinium salt, 4-[[4-(dimethylamino)-2,3,5,6-tetrafluorophenyl]ethynyl]-2,3,5,6-tetrafluoro-1-methyl

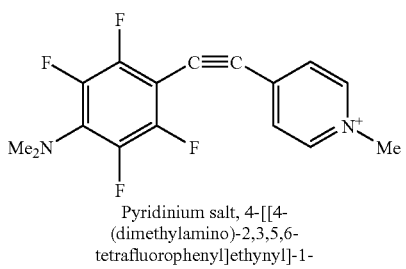

Pyridinium salt, 4-[[4-(dimethylamino)-2,3,5,6-tetrafluorophenyl]ethynyl]-1-methyl-

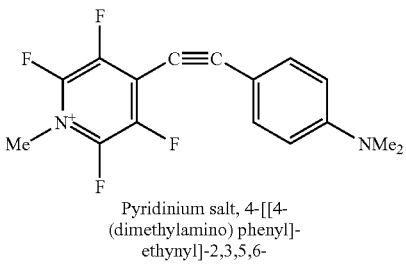

Pyridinium salt, 4-[[4-(dimethylamino) phenyl]-ethynyl]-2,3,5,6-tetrafluoro-1-methyl-

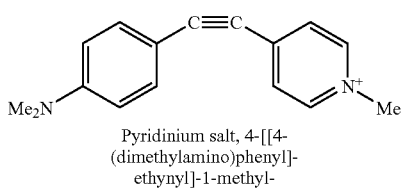

Pyridinium salt, 4-[[4-(dimethylamino)phenyl]-ethynyl]-1-methyl-

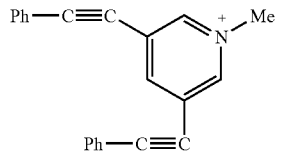

Pyridinium iodide, 1-methyl-3,5-bis(phenylethynyl)

-continued

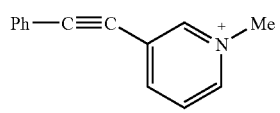

Pyridinium iodide, 1-methyl-3-(phenylethynyl)

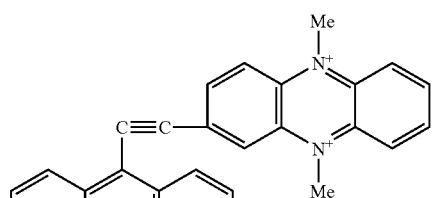

Phenazinium salt, 2,2'-(9,10-anthracenediyldi-2,1-ethynediyl)bis[5,10-dimethyl

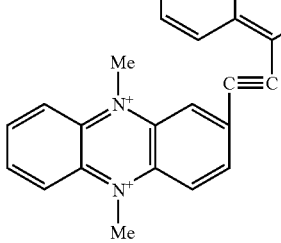

Salt of trifluoromethanesulfonic acid and of pyridinium, 1-methyl-2-(phenylethynyl)

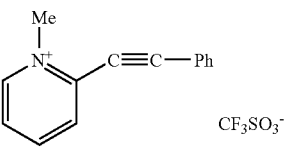

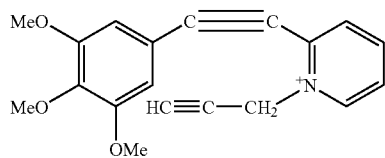

CF$_3$SO$_3^-$

Salt of trifluoromethanesulfonic acid (1:1) and of pyridinium, 1-(2-propynyl)-2-[(3,4,5-trimethoxyphenyl)ethynyl]

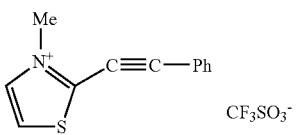

Salt of trifluoromethanesulfonic acid (1:1) and of thiazolium, 3-methyl-2-(phenylethynyl)

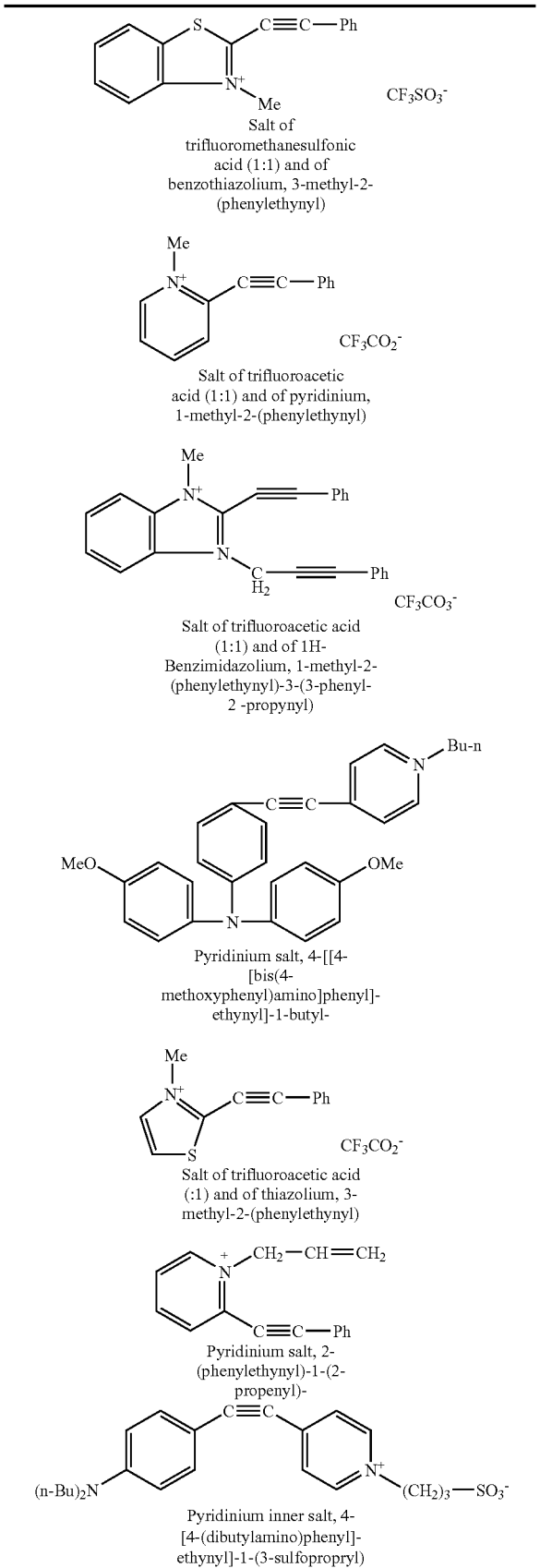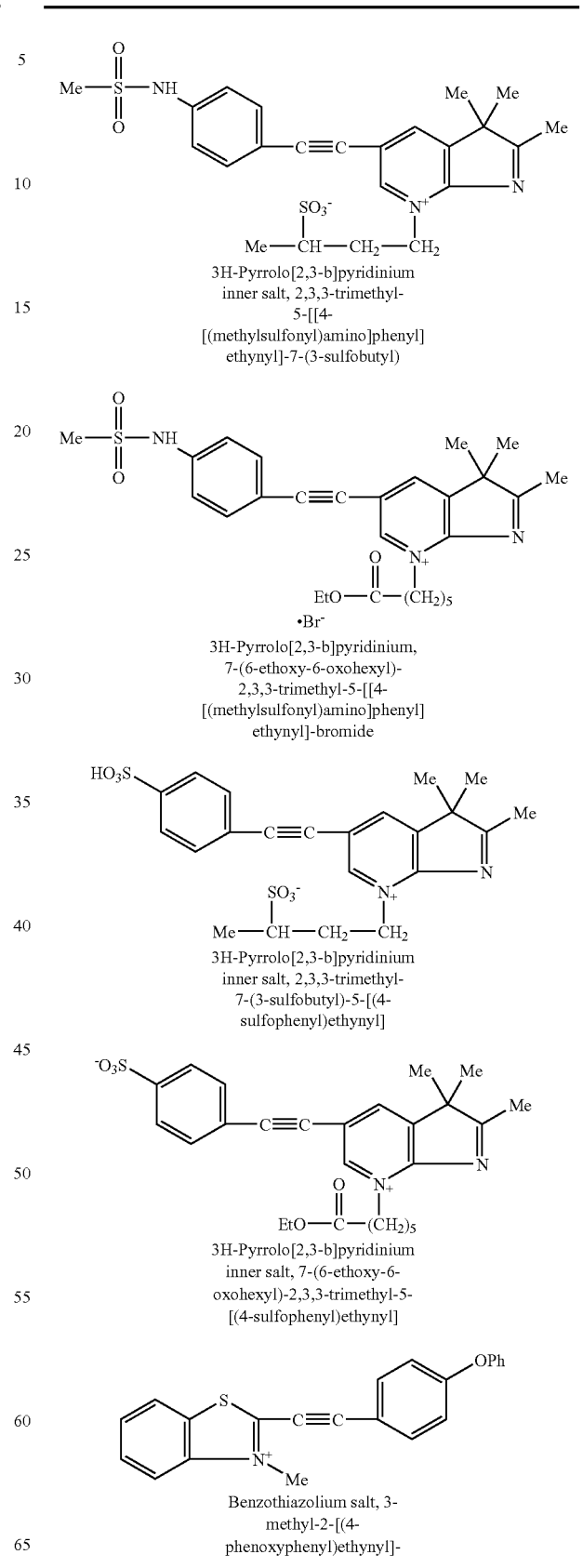

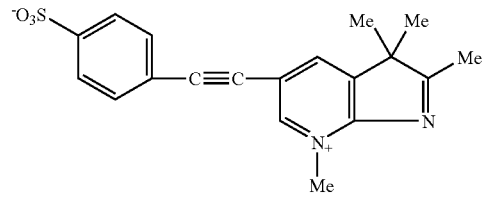

3H-Pyrrolo[2,3-b]pyridinium
inner salt, 2,3,3,7-
tetramethyl-5-[(4-
sulfophenyl)ethynyl]

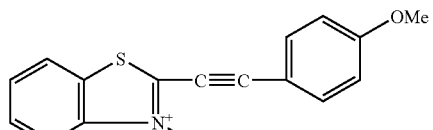

Benzothiazolium salt, 2[(4-
methoxyphenyl)ethynyl]-3-
methyl

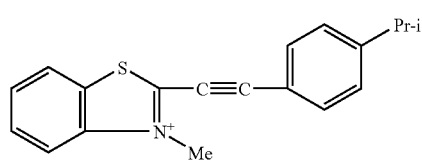

Benzothiazolium salt, 3-
methyl-2-[[4-(1-
methylethyl)phenyl]ethynyl]-

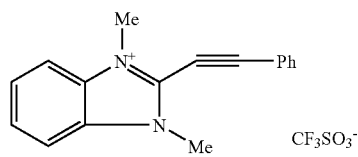

Salt of
trifluoromethanesulfonic acid
(1:1) and of
1H-Benzimidazolium,1,3-
dimethyl-2-(phenylethynyl)

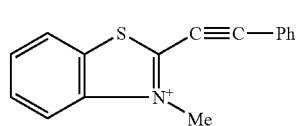

Benzothiazolium salt, 3-
methyl-2-(phenylethynyl)-

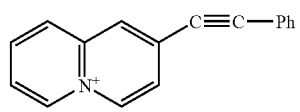

Salt of 2,4,6-trinitrophenol
(1:1) and of quinolizinium,
2-(phenylethynyl)

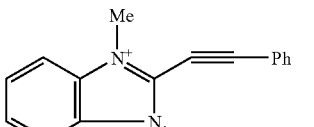

Salt of
trifluoromethanesulfonic
acid (1:1) 1H-
Benzimidazolium, 1-methyl-2-
(phenylethynyl)-3-(3-phenyl-
2-propynyl)

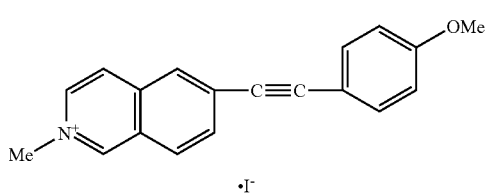

Isoquinolinium iodide, 6-[(4-
methoxyphenyl)ethynyl]-2-
methyl

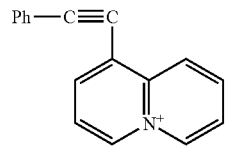

Salt of 2,4,6-trinitrophenol
(1:1) and of quinolizinium,
1-(phenylethynyl)

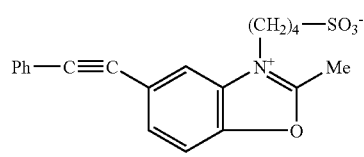

Benzoxazolium inner salt, 2-
methyl-5-(phenylethynyl)-3-
(4-sulfobutyl)

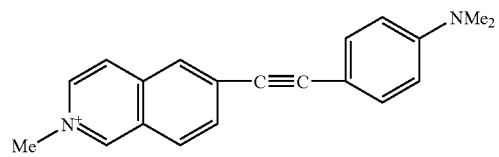

Isoquinolinium iodide, 6-
[[4-(dimethylamino)phenyl]-
ethynyl]-2-methyl

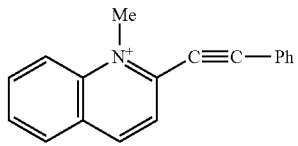

Salt of
trifluoromethanesulfonic acid
(1:1) and of quinolinium, 1-
methyl-2-(phenylethynyl)

-continued

Isoquinolinium iodide, 2-methyl-6-(phenylethynyl)

Salt of trifluoromethanesulfonic acid (1:1) and of 3H-Indolium, 1,3,3,-trimethyl-2-(phenylethynyl)

Benzothiazolium inner salt, 2-methyl-5-(phenylethynyl)-3-(4-sulfobutyl)

Pyridinium methyl sulfate, 4-[(4-chlorophenyl)ethynyl]-1-methyl-, methyl sulfate Salt of trifluoromethanesulfonic acid (1:1) and of b Benzothiazolium, 2-[(4-chlorophenyl)ethynyl]-3-methyl-, Pyridinium bromide, 4-[(4-bromophenyl)ethynyl]-1-docosyl Pyridinium methyl sulfate, 4-[(4-bromophenyl)ethynyl]-1-methyl- -continued Pyridinium perchlorate, 1-butyl-3,5-dimethyl-2,6-diphenyl-4-(phenylethynyl)

Pyridinium bromide, 4-[(4-bromophenyl)ethynyl]-1-dodecyl

Pyridinium bromide, 4-[(4-methoxyphenyl)ethynyl]-1-octadecyl

Pyridinium perchlorate, 3,5-dimethyl-2,6-diphenyl-4-(phenylethynyl)-1-(phenylmethyl)

Pyridinium bromide, 1-docosyl-4-[(4-methoxyphenyl)ethynyl]

Pyridinium perchlorate, 1,3,5-trimethyl-2,-diphenyl-4-(phenylethylnyl)

-continued

Pyridinium bromide, 1-docosyl-4-(phenylethynyl)

Pyridinium bromide, 1-decyl-4-[(4-methoxyphenyl)ethynyl]

1-Methyl-4-phenylethynylpyridinium perchlorate

Pyridinium bromide, 1-octadecyl-4-(phenylethynyl)

1-Methyl-2,6-bis(phenylethynyl)pyridinium perchlorate

1-Methyl-2-phenylethynylquinolinium para-toluenesulfonate

-continued

1-Ethyl-2-phenylethynylquinolinium perchlorate

1-Methyl-2-phenylethynylpyridinium perchlorate

Salt of 1-Methyl-4-phenylethynylpyridinium methyl

1-Methyl-2-phenylethynylquinolinium perchlorate

Pyridinium bromide, 2-methyl-1-(2-oxo-2-phenylethyl)-6-(phenylethynyl)

Methyl-2-phenylethynylpyridinium methyl sulfate

-continued

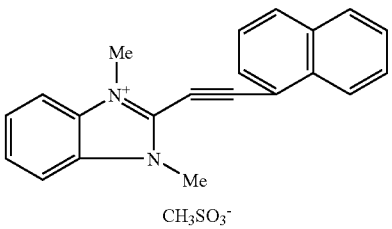

CH₃SO₃⁻

1H-Benzimidazolium 1,3-dimethyl-2-(1-naphthalenylethynyl)methyl sulfate

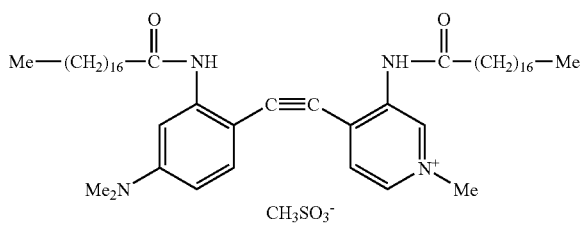

CH₃SO₃⁻

Pyridinium methyl sulfate, 4-[[4-(dimethylamino)-2-[(1-oxooctadecyl)amino]phenyl]-ethynyl]-1-methyl-3-[(1-oxooctadecyl)amino]

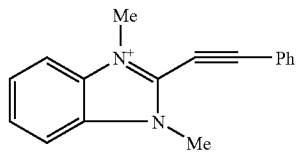

I⁻

Benzimidazolium iodide, 1,3-dimethyl-2-(phenylethynyl)-,

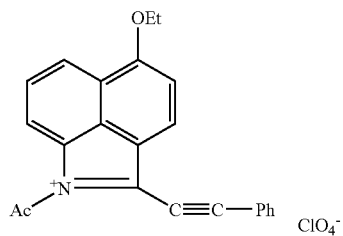

ClO₄⁻

Benz[cd]indolium perchlorate, 1-acetyl-5-ethoxy-2-(phenylethynyl)

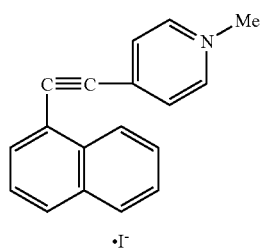

·I⁻

Pyridinium iodide, 1-methyl-4-(1-naphthalenylethynyl)-,

-continued

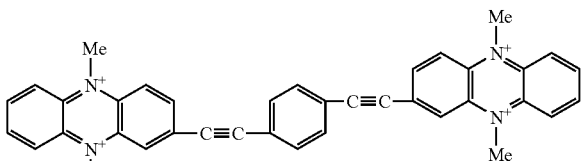

Phenazinium salt, 2,2'-(1,4-phenylenedi-2,1-ethynediyl)bis[5,10-dimethyl-

The anions mentioned in the above table are given merely as examples.

The direct dye(s) of formula (I), (II) or (III) more particularly represent from 0.01% to 20% by weight and preferably from 0.1% to 5% by weight relative to the total weight of the composition.

The composition may also comprise at least one oxidation base.

The oxidation bases are chosen, for example, from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-p-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)-pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-($\beta$-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present invention are the 3-aminopyrazolo[1,5-a]-pyridine oxidation bases or addition salts thereof described, for example, in patent application FR 2 801 308. Examples that may be mentioned include pyrazolo[1,5-a]pyrid-3-ylamine, 2-acetylaminopyrazolo-[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamino, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]-ethanol, 2-[(3-aminopyrazolo[1,5-a]pyrid-7-yl)(2-hydroxyethyl)amino]ethanol, 3-aminopyrazolo[1,5-a]-pyridin-5-ol, 3-aminopyrazolo[1,5-a]pyridin-4-ol, 3-aminopyrazolo[1,5-a]pyridin-6-ol and 3-aminopyrazolo-[1,5-a]pyridin-7-ol, and the addition salts thereof.

Among the pyrimidine derivatives that may be mentioned are the compounds described, for example, in patents DE 2 359 399; JP 88-169 571; JP 05-63124; EP 0 770 375 or patent application WO 96/15765, for instance 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof, and the tautomeric forms thereof, when a tautomeric equilibrium exists.

Among the pyrazole derivatives that may be mentioned are the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-($\beta$-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-($\beta$-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-($\beta$-hydroxyethyl)amino-1-methylpyrazole, and the addition salts thereof. 4,5-Diamino-1-($\beta$-methoxyethyl)pyrazole may also be used.

The oxidation base(s) present in the composition of the invention is (are) generally present in an amount ranging from 0.001% to 20% by weight approximately, and preferably ranging from 0.005% to 6%, relative to the total weight of the dye composition.

If the composition contains at least one oxidation base, this base is optionally and preferably combined with one or more couplers. Among the couplers that may be used are those conventionally used for the dyeing of keratin fibres. Mention may be made especially of meta-phenylenediamines, meta-aminophenols, meta-diphenols, naphthalene-based couplers and heterocyclic couplers, and also the addition salts thereof.

Mention may be made, for example, of 1,3-dihydroxybenzene, 1,3-dihydroxy-2-methylbenzene, 4-chloro-1,3-dihydroxybenzene, 2,4-diamino-1-($\beta$-hydroxyethyloxy)benzene, 2-amino-4-($\beta$-hydroxyethylamino) 1-methoxybenzene, 1,3-diaminobenzene, 1,3-bis(2,4-diaminophenoxy)propane, 3-ureidoaniline, 3-ureido-1-dimethylaminobenzene, sesamol, 1-$\beta$-hydroxyethylamino-3,4-methylenedioxybenzene, $\alpha$-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-($\beta$-hydroxyethyl)amino-3,4-methylenedioxybenzene, 2,6-bis($\beta$-hydroxyethylamino)toluene, 6-hydroxyindoline, 2,6-dihydroxy-4-methylpyridine, 1-H-3-methylpyrazo-5-one, 1-phenyl-3-methylpyrazo-5-one, 2,6-dimethyl-pyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In the composition of the present invention, the coupler(s) is (are) generally present in an amount ranging from 0.001% to 20% and preferably ranging from 0.005% to 6% by weight approximately relative to the total weight of the dye composition.

In general, the addition salts of the oxidation bases and couplers that may be used in the context of the invention are especially chosen from the addition salts with an acid such as the hydrochlorides, hydrobromides, sulfates, citrates, succinates, tartrates, lactates, tosylates, benzenesulfonates, phosphates and acetates.

The dye composition in accordance with the invention may also contain one or more additional direct dyes other than the direct dyes of formula (I), (II) or (III) according to the invention, which may be chosen especially from neutral, acidic or cationic nitrobenzene dyes, neutral, acidic or cationic azo, azomethine or methine direct dyes, neutral, acidic or cationic quinone and in particular anthraquinone, naphthoquinone or benzoquinone direct dyes, azine direct dyes, triarylmethane direct dyes, indoamine direct dyes, tetraazapentamethine, phenothiazine, indigoid, xanthene, phenanthridine and phthalocyanin dyes, and natural direct dyes, alone or as mixtures.

Among the benzene-based direct dyes that may be used according to the invention, mention may be made, in a non-limiting manner, of the following compounds:

1,4-diamino-2-nitrobenzene
1-amino-2-nitro-4-β-hydroxyethylaminobenzene
1-amino-2-nitro-4-bis(β-hydroxyethyl)aminobenzene
1,4-bis(β-hydroxyethylamino)-2-nitrobenzene
1-β-hydroxyethylamino-2-nitro-4-bis(β-hydroxyethylamino)benzene
1-β-hydroxyethylamino-2-nitro-4-aminobenzene
1-β-hydroxyethylamino-2-nitro-4-(ethyl)(β-hydroxyethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-tris(hydroxymethyl)methylamino-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-4-β,γ-dihydroxypropyloxy-2-nitrobenzene
1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis(β-hydroxyethyl)amino-3-nitrobenzene
1-β-hydroxyethylamino-2-nitrobenzene
1-hydroxy-4-β-hydroxyethylamino-3-nitrobenzene.

Among the azo, azomethine or methine direct dyes that may be used according to the invention, mention may be made of the cationic dyes described in patent applications WO 95/15144, WO 95/01772 and EP-714 954, the content of which forms an integral part of the invention.

Among these compounds, the ones that may be mentioned most particularly are the following dyes, and also other cosmetically acceptable salts of these compounds:
1,3-dimethyl-2-[[4-(dimethylamino)phenyl]azo]-1H-imidazolium chloride,
1,3-dimethyl-2-[(4-aminophenyl)azo]-1H-imidazolium chloride,
1-methyl-4-[(methylphenylhydrazono)methyl]pyridinium methyl sulfate.

Among the azo direct dyes that may also be mentioned are the following dyes, described in the Color Index International, 3rd edition:
Disperse Red 17
Acid Yellow 9
Acid Black 1
Basic Red 22
Basic Red 76
Basic Yellow 57
Basic Brown 16
Acid Yellow 36
Acid Orange 7
Acid Red 33
Acid Red 35
Basic Brown 17
Acid Yellow 23
Acid Orange 24
Disperse Black 9.

Mention may also be made of 1-(4'-aminodiphenylazo)-2-methyl-4-bis(β-hydroxyethyl)aminobenzene and 4-hydroxy-3-(2-methoxyphenylazo)-1-naphthalenesulfonic acid.

Among the quinone direct dyes that may be mentioned are the following dyes:
Disperse Red 15
Solvent Violet 13
Acid Violet 43
Disperse Violet 1
Disperse Violet 4
Disperse Blue 1
Disperse Violet 8
Disperse Blue 3
Disperse Red 11
Acid Blue 62
Disperse Blue 7
Basic Blue 22
Disperse Violet 15
Basic Blue 99 and also the following compounds:
1-N-methylmorpholiniumpropylamino-4-hydroxyanthraquinone
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis(β,γ-dihydroxypropylamino)anthraquinone.

Among the azine dyes that may be mentioned are the following compounds:
Basic Blue 17
Basic Red 2.

Among the triarylmethane dyes that may be used according to the invention, mention may be made of the following compounds:
Basic Green 1
Acid blue 9
Basic Violet 3
Basic Violet 14
Basic Blue 7
Acid Violet 49
Basic Blue 26
Acid Blue 7.

Among the indoamine dyes that may be used according to the invention, mention may be made of the following compounds:
2-β-hydroxyethylamino-5-[bis(β-4'-hydroxyethyl)amino]anilino-1,4-benzoquinone
2-β-hydroxyethylamino-5-(2'-methoxy-4'-amino)anilino-1,4-benzoquinone
3-N-(2'-chloro-4'-hydroxy)phenylacetylamino-6-methoxy-1,4-benzoquinone imine
3-N-(3'-chloro-4'-methylamino)phenylureido-6-methyl-1,4-benzoquinone imine
3-[4'-N-(ethyl, carbamylmethyl)amino]phenylureido-6-methyl-1,4-benzoquinone imine.

Among the dyes of tetraazapentamethine type that may be used according to the invention, mention may be made of the following compounds given in the table below, An being defined as previously:

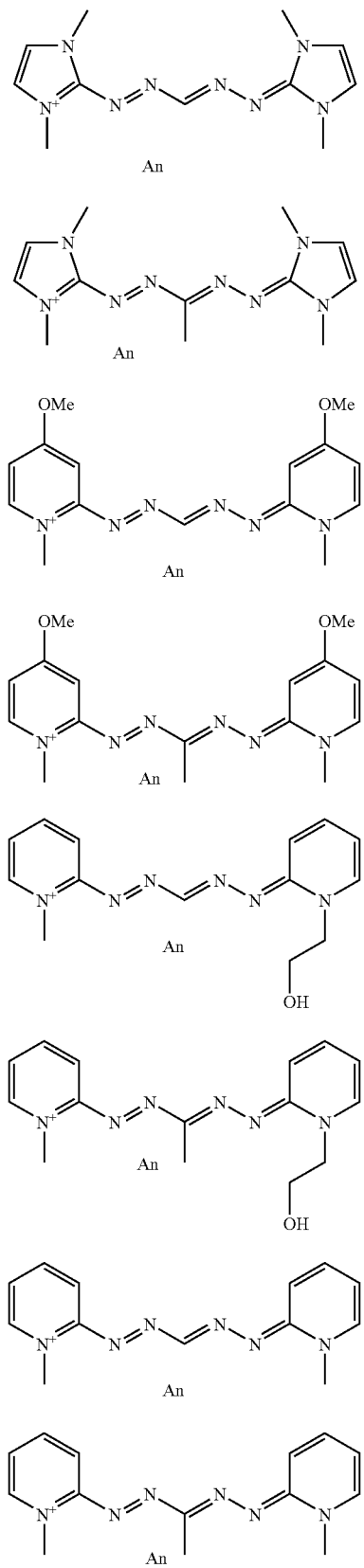

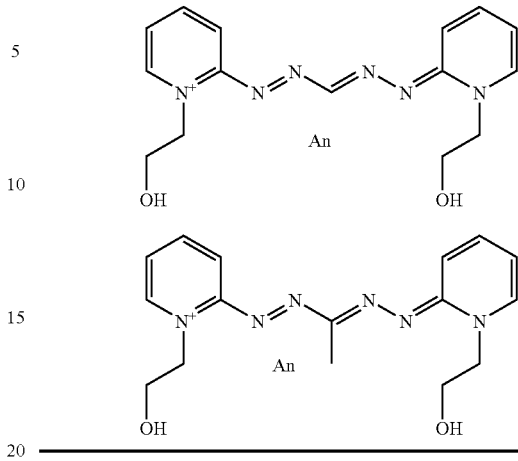

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin and apigenidin. It is also possible to use extracts or decoctions containing these natural dyes, and especially henna-based poultices or extracts.

The additional direct dye(s) other than those of formula (I) preferably represent(s) from 0.001% to 20% by weight approximately, and even more preferentially from 0.005% to 10% by weight approximately, relative to the total weight of the composition.

The composition according to the invention may also comprise at least one oxidizing agent conventionally used for the oxidation dyeing of keratin fibres, for instance hydrogen peroxide, urea peroxide, alkali metal bromates, persalts such as perborates and persulfates, peracids and oxidase enzymes, among which mention may be made of peroxidases, 2-electron oxidoreductases such as uricases, and 4-electron oxygenases, for instance laccases. Hydrogen peroxide is particularly preferred.

The cosmetically acceptable medium is generally constituted of water or of a mixture of water and of at least one organic solvent.

Examples of organic solvents that may be mentioned include linear or branched $C_1$-$C_4$ alkanols, such as ethanol and isopropanol; glycerol; glycols and glycol ethers, for instance 2-butoxyethanol, propylene glycol, dipropylene glycol, propylene glycol monomethyl ether, diethylene glycol monomethyl ether and monoethyl ether, and also aromatic alcohols, for instance benzyl alcohol or phenoxyethanol, similar products and mixtures thereof.

The solvent(s) may be present in proportions preferably ranging from 1% to 40% by weight approximately, and even more preferentially from 5% to 30% by weight approximately, relative to the total weight of the dye composition.

The pH of the composition in accordance with the invention is generally between 3 and 12 approximately, and preferably between 4 and 10 approximately. It may be adjusted to the desired value by means of acidifying or basifying agents usually used in the field.

Among the acidifying agents that may be mentioned, for example, are mineral or organic acids, for instance hydrochloric acid, orthophosphoric acid, sulfuric acid, carboxylic acids, for instance acetic acid, tartaric acid, citric acid or lactic acid, and sulfonic acids.

Among the basifying agents that may be mentioned, for example, are aqueous ammonia, alkali metal carbonates, alkanolamines such as monoethanolamine, diethanolamine and triethanolamine, and also derivatives thereof, sodium hydroxide, potassium hydroxide and the compounds of formula (II) below:

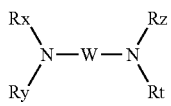

in which W is a propylene residue optionally substituted with a hydroxyl group or a $C_1$-$C_6$ alkyl radical; Rx, Ry, Rz and Rt, which may be identical or different, represent hydrogen atom or a $C_1$-$C_6$ alkyl or $C_1$-$C_6$ hydroxyalkyl radical.

According to one particularly advantageous embodiment, the composition comprises one or more surfactants. These surfactants may be chosen, without preference, alone or as mixtures, from anionic, amphoteric, nonionic, zwitterionic and cationic surfactants.

As regards the anionic surfactants, use is usually made of the salts, in particular the alkali metal salts such as the sodium salts, the ammonium salts, the amine salts, the amino alcohol salts or the alkaline-earth metal salts, for example of magnesium, of the following compounds, alone or as a mixture:
  alkyl sulfates, alkyl ether sulfates, alkylamido ether sulfates, alkylarylpolyether sulfates;
  alkylsulfonates, alkylamidesulfonates, alkylarylsulfonates;
  alkylsulfosuccinates, alkyl ether sulfosuccinates, alkylamidesulfosuccinates;
  alkylsulfoacetates;
  acylsarcosinates; and acylglutamates;
  alkyl esters of polyglycosidecarboxylic acids such as alkyl glucoside citrates, alkyl polyglycoside tartrates and alkyl polyglycoside sulfosuccinates;
  alkylsulfosuccinamates;
  acylisethionates, N-acyltaurates; acyllactylates;
  alkyl-D-galactoside uronic acids;
  polyoxyalkylenated alkyl ether carboxylic acids, polyoxyalkylenated alkylaryl ether carboxylic acids, polyoxyalkylenated alkylamido ether carboxylic acids;
  the alkyl or acyl (RCO—) group of these compounds containing from 10 to 24 carbon atoms and the aryl group preferably denoting a phenyl or benzyl group; the number of oxyalkylene, and preferably oxyethylene, groups is between 2 and 50.

As regards the nonionic surfactants, they may be advantageously chosen from the following compounds, alone or as a mixture:
  polyethoxylated, polypropoxylated or polyglycerolated fatty alcohols,
  polyethoxylated, polypropoxylated or polyglycerolated alpha-diols,
  the number of ethylene oxide or propylene oxide groups ranging from 2 to 50; the number of glycerol groups ranging from 2 to 30;
  condensates of ethylene oxide and of propylene oxide on fatty alcohols;
  polyethoxylated fatty amides containing from 2 to 30 mol of ethylene oxide;
  polyglycerolated fatty amides containing from 1 to 5 glycerol groups;
  polyethoxylated fatty amines containing from 2 to 30 mol of ethylene oxide;
  ethoxylated fatty acid esters of sorbitan containing from 2 to 30 mol of ethylene oxide, fatty acid esters of sucrose;
  alkylpolyglucosides, N-alkylglucamine derivatives;
  these compounds comprising at least one alkyl or alkenyl chain containing from 10 to 24 carbon atoms;
  copolymers of ethylene oxide and of propylene oxide.

The cationic surfactants included in the composition according to the invention may be chosen especially from the following compounds, alone or as a mixture:
  optionally polyethoxylated (2 to 30 mol of ethylene oxide) primary, secondary or tertiary fatty amines, and salts thereof,
  quaternary ammonium salts such as tetraalkylammonium, alkylamidoalkyltrialkylammonium, trialkylbenzylammonium, trialkylhydroxyalkylammonium or alkylpyridinium chlorides or bromides,
  alkylimidazoline derivatives;
  these compounds comprising at least one alkyl chain containing from 10 to 24 carbon atoms.

Finally, the amphoteric surfactants may be chosen from the following compounds, alone or as a mixture:
  secondary or tertiary aliphatic amine derivatives, in which the aliphatic group is a linear or branched chain containing from 10 to 24 carbon atoms and comprising at least one water-solubilizing anionic group, for instance a carboxylate, sulfonate, sulfate, phosphate or phosphonate group,
  alkylbetaines, sulfobetaines, alkylamido($C_6$-$C_8$)alkylbetaines, alkylamido($C_6$-$C_8$)alkylsulfobetaines;
  these compounds comprising at least one alkyl chain containing from 10 to 24 carbon atoms.

Preferably, the surfactants are nonionic, anionic or amphoteric, and even more preferably nonionic.

Usually, the surfactants are present in an amount of between 0.01% and 50% by weight and preferably between 0.1% and 25% by weight relative to the total weight of the composition.

The cosmetic composition in accordance with the invention may also comprise one or more adjuvants conventionally used in cosmetic compositions especially for dyeing human keratin fibres, such as anionic, cationic, nonionic, amphoteric or zwitterionic polymers, or mixtures thereof; mineral thickeners; antioxidants; penetrants; sequestrants; fragrances; buffers; dispersants; conditioning agents, for instance cations, cationic or amphoteric polymers, chitosans and volatile or non-volatile, modified or unmodified silicones; film-forming agents; ceramides; preserving agents; stabilizers; opacifiers.

The above adjuvants are generally present in an amount for each of them of between 0.01% and 20% by weight relative to the weight of the composition.

Preferably, the composition according to the invention comprises at least one polymer.

The composition according to the invention may be in various forms, such as in the form of liquids, shampoos, creams or gels, or in any other suitable form.

Another subject of the invention consists of a process for treating human keratin fibres, in which the composition according to the invention is applied to the said fibres.

According to a first variant, a composition as defined is applied to the said wet or dry fibres, for a sufficient time, after which the resulting fibres are optionally shampooed, rinsed again and dried or left to dry.

According to a second variant of the process, a composition as defined is applied to the said wet or dry fibres without final rinsing.

The first variant may be used for compositions of any type, whether or not they comprise an oxidizing agent and/or an additional direct dye and/or an oxidation base optionally combined with a coupler.

The second variant is particularly suitable for compositions not comprising any oxidation dye (oxidation base and optionally coupler) or any oxidizing agent.

In the case of the first variant of the process, the application time is usually sufficient to develop the desired colouration and/or lightening.

As a guide, the duration of application of the composition is from about 1 to 60 minutes and more particularly from about 2 to 30 minutes.

Moreover, the temperature at which the process according to the invention is performed is generally between room temperature (15 to 25° C.) and 60° C. and more particularly between 15 and 45° C.

When the composition comprises an oxidizing agent, the process according to the invention includes a preliminary step that consists in separately storing, on the one hand, a composition comprising, in a cosmetically acceptable medium, at least one cationic direct dye comprising at least one carbon-carbon triple bond and more particularly at least one dye of formula (I), (II) or (III), optionally at least one additional direct dye and/or optionally at least one oxidation base optionally combined with at least one coupler, and, on the other hand, a composition comprising, in a cosmetically acceptable medium, at least one oxidizing agent, and then in mixing them together at the time of the use. It should be noted that the direct dye(s) according to the invention, the additional direct dye(s) and the base(s) and optionally the coupler(s) may be stored separated from each other or partially combined (the direct dyes together or the additional direct dye(s) with the base(s) and/or the coupler(s), for example).

Once the mixture has been prepared, the process according to the invention is performed in accordance with what has been mentioned previously.

Another subject of the invention is a multi-compartment device, comprising at least one compartment containing a composition comprising at least one cationic direct dye comprising at least one carbon-carbon triple bond and more particularly at least one dye of formula (I), (II) or (III), and at least one other compartment containing a composition comprising at least one oxidizing agent.

This device may be equipped with a means for applying the desired mixture onto the hair, such as the devices described in patent FR 2 586 913.

It should be noted that, when the composition contains at least one additional direct dye and/or at least one oxidation base optionally combined with at least one coupler (oxidation dye precursor(s)), this or these compound(s) may be in the same compartment as that of the cationic dye(s) comprising at least one carbon-carbon triple bond and more advantageously at least one dye of formulae (I), (II) and/or (III), or alternatively in a third compartment, or else each in a different compartment. It may also be envisaged to place the direct dyes according to the invention with the additional direct dye(s) in the same compartment and the oxidation dye precursor(s) (base(s) and optionally coupler(s)) in a different compartment.

The examples that follow are intended to illustrate the invention without, however, limiting its scope.

EXAMPLE 1

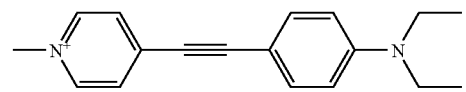

The compound whose structure is given above is used in the following formulation:

| Dye | 0.5% |
| --- | --- |
| (50/50 C8/C10)alkyl polyglucoside | 5% |
| PEG-8 | 6% |
| Benzyl alcohol | 4% |
| Hydroxyethyl cellulose (MW 720 000) | 2% |
| pH 9 buffer | 50% |
| Water | qs 100 |

This mixture is applied for 30 minutes at room temperature to locks of natural 90% grey hair and permanent-waved 90% grey hair.

After the application, the locks are rinsed, shampooed and then dried. They are dyed a strong coppery colour.

Even on reducing the leave-in time to 5 minutes, a sufficiently strong shade is still obtained.

Similar formulations were prepared by replacing the pH 9 buffer with pH 4 and pH 7 buffers.

A strong coppery colour is obtained each time.

They show good colour uptake also in lightening medium, with good light-fastness.

EXAMPLE 2

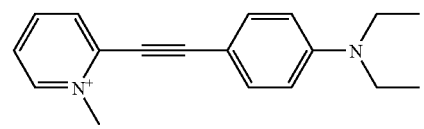

The compound whose structure is given above is used in the following formulation:

| Dye | 0.5% |
| --- | --- |
| (50/50 C8/C10)alkyl polyglucoside | 5% |
| PEG-8 | 6% |
| Benzyl alcohol | 4% |
| Hydroxyethylcellulose (MW 720 000) | 2% |
| pH 9 buffer | 50% |
| Water | qs 100 |

This mixture is applied for 30 minutes at room temperature to locks of natural 90% grey hair and permanent-waved 90% grey hair.

After the application, the locks are rinsed, shampooed and then dried.

They are dyed a strong golden-coppery colour.

Even on reducing the leave-in time to 5 minutes, a sufficiently strong shade is still obtained.

Similar formulations were prepared by replacing the pH 9 buffer with pH 4 and pH 7 buffers.

A strong coppery colour is obtained each time.

They show good colour uptake also in lightening medium, with good light-fastness.

The invention claimed is:

1. A composition for dyeing human keratin fibers comprising, in a cosmetically acceptable medium, at least one direct dye chosen from direct dyes of formulae (I), (II) and (III):

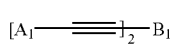 (I)

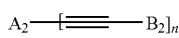 (II)

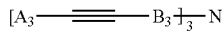 (III)

wherein:

$A_1$, $A_2$ and $A_3$, independently of each other, are chosen from cationic heterocyclic groups comprising at least one quaternized nitrogen and optionally fused with at least one aromatic nucleus, and wherein $A_1$, $A_2$ and $A_3$ are attached to the at least one C≡C functional group via one of the carbon atoms of the cationic heterocycle or via the at least one aromatic nucleus to which the cationic heterocycle is optionally fused; and wherein said at least one quaternized nitrogen atom optionally bears at least one radical chosen from amino radicals; $C_2$-$C_{20}$ acyl radicals; and $C_1$-$C_{25}$ alkyl radicals optionally substituted with at least one radical chosen from phenyl, phenyl-carbonyl, ($C_1$-$C_4$)alkoxycarbonyl, sulfo (—$SO_3M$, wherein M is chosen from a hydrogen atom and alkali metals), ethylenyl (—CH═$CH_2$), acetylenyl (—C≡CH), and phenyl-acetylenyl (—C≡C—$C_6H_5$);

$A_1$, $A_2$ and $A_3$ may be optionally substituted, beyond the radicals borne by the quaternized nitrogen atoms, with at least one radical chosen from halogen atoms, $C_1$-$C_{25}$ alkyl radicals, ($C_1$-$C_4$) alkoxy radicals, ($C_1$-$C_{20}$)alkylcarbonylamino radicals, and phenyl radicals;

$B_1$, $B_2$ and $B_3$, independently of each other, are aromatic nucleuses chosen from phenyl groups, anthracenyl groups, and naphthyl groups, attached to one or two C≡C functional groups;

$B_1$, $B_2$ and $B_3$ may be optionally substituted with at least one group chosen from:

amino groups optionally bearing one or two radicals, independently of each other, chosen from $C_1$-$C_{18}$ alkyl, ($C_1$-$C_{20}$)alkylcarbonyl, ($C_1$-$C_{20}$)alkylsulfonyl, and phenyl optionally substituted with a $C_1$-$C_4$ alkoxy group;

hydroxyl;

$C_1$-$C_4$ alkoxy;

$C_1$-$C_{10}$ alkyl optionally bearing an amino group;

phenoxy;

sulfo (—$SO_3M$, wherein M is chosen from a hydrogen atom and alkali metals);

cyano;

trifluoromethyl;

halogen chosen from chlorine, fluorine and bromine; and acetylthio ($CH_3$—CO—S—);

n is equal to 1 or 2;

the electrical neutrality of the at least one direct dye being optionally assured via at least one cosmetically acceptable anion;

and wherein the composition also comprises at least one surfactant present in an amount ranging from 0.01% to 50% by weight relative to the total weight of the composition, and chosen from anionic, amphoteric, nonionic, zwitterionic and cationic surfactants.

2. The composition according to claim 1, wherein, $A_1$, $A_2$ and $A_3$, independently of each other, are cationic heterocyclic groups comprising at least one quaternized nitrogen, optionally fused with at least one aromatic nucleus, chosen from pyridinium, (benz)imidazolium, (benzo)thiazolium, benzoxazolium, (iso)quinolinium, (benz)indolium, acridinium, quinolizinium, phenazinium, and pyrrolopyridinium groups.

3. The composition according to claim 1, wherein the at least one direct dye is chosen from direct dyes of formula (I) and further wherein said $A_1$ is chosen from phenazinium groups.

4. The composition according to claim 1, wherein $B_1$ is an anthracenyl group.

5. The composition according to claim 1, wherein the at least one direct dye is chosen from direct dyes of formula (II), and further wherein:

n is 1; and $A_2$ is chosen from optionally substituted pyridinium, benzimidazolium, (benzo)thiazolium, benzoxazolium, (iso)quinolinium, (benz)indolium, acridinium, thioxanthilium, quinolizinium and pyrrolopyridinium groups.

6. The composition according to claim 1, wherein the at least one direct dye is of chosen from direct dyes of formula (II), and further wherein:

n is 2; and $A_2$ is chosen from pyridinium groups.

7. The composition according to claim 1, wherein $B_2$, independently of each other, is chosen from optionally substituted phenyl groups and naphthyl groups.

8. The composition according claim 1, wherein the at least one direct dye is of chosen from direct dyes of formula (III), and further wherein $A_3$ is chosen from pyridinium groups.

9. The composition according to claim 1, wherein $B_3$ is chosen from phenyl groups.

10. A composition for dyeing human keratin fibers comprising, in a cosmetically acceptable medium, at least one direct dye chosen from:

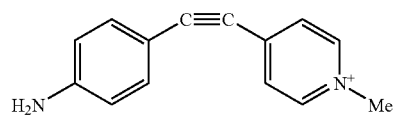

Pyridinium salt, 4-[(4-aminophenyl)ethynyl]-1-methyl

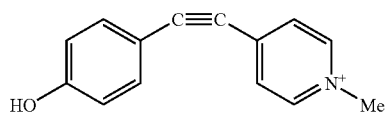

Pyridinium salt, 4-[(4-hydroxyphenyl)ethynyl]-1-methyl

-continued

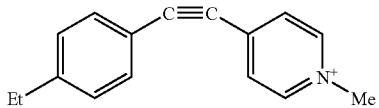

Pyridinium salt, 4-[(4-ethylphenyl)ethynyl]-1-methyl-

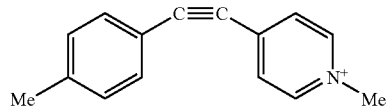

Pyridinium salt, 1-methyl-4-[(4-methylphenyl)ethynyl]

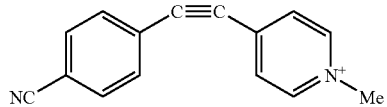

Pyridinium salt, 4-[(4-cyanophenyl)ethynyl]-1-methyl

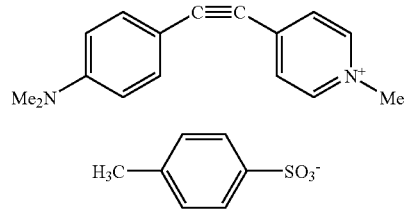

Salt of 4-methylbenzenesulfonic acid (1:1) and of pyridinium, 4-[[4-(dimethylamino)phenyl]ethynyl]-1-methyl-, monohydrate

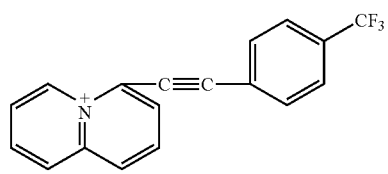

Quinolizinium salt, 4-[[4-(trifluoromethyl)phenyl]ethynyl]-

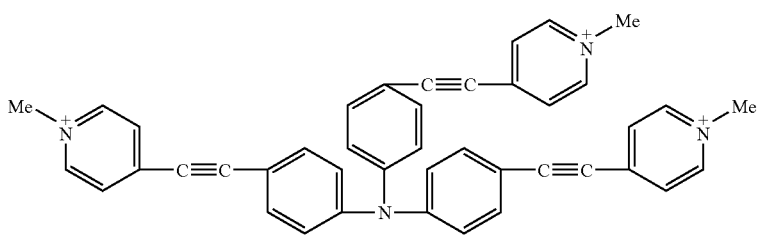

Pyridinium trichloride, 4,4',4''-[nitrilotris(4,1-phenylene-2,1-ethynediyl)]tris[1-methyl-, trichloride

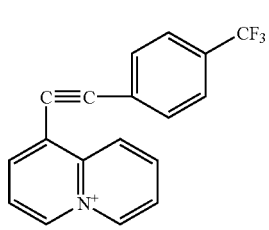

Quinolizinium salt, 1-[[4-(trifluoromethyl)phenyl]ethynyl]-

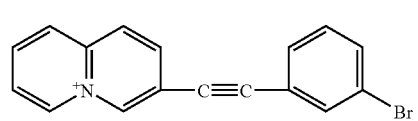

Quinolizinium salt, 3-[(3-bromophenyl)ethynyl]-

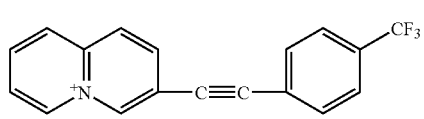

Quinolizinium salt, 3-[[4-(trifluoromethyl)phenyl]ethynyl]-

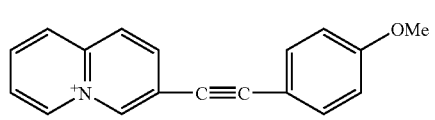

Quinolizinium salt, 3-[(4-methoxyphenyl)ethynyl]-

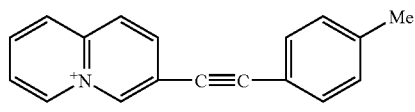

Quinolizinium salt, 3-[(4-methylphenyl)ethynyl]-

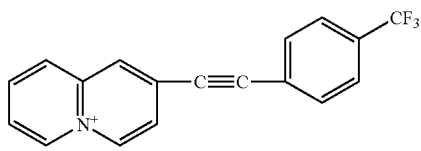

Quinolizinium salt, 2-[[4-(trifluoromethyl)phenyl]ethynyl]

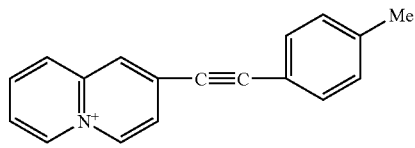

Quinolizinium salt, 2-[(4-methylphenyl)ethynyl]-

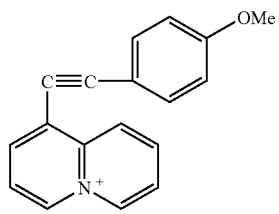

Quinolizinium salt, 1-[(4-methoxyphenyl)ethynyl]-

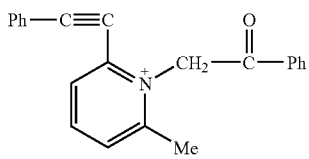

Pyridinium salt, 2-methyl-1-(2-oxo-2-phenylethyl)-6-(phenylethynyl)-

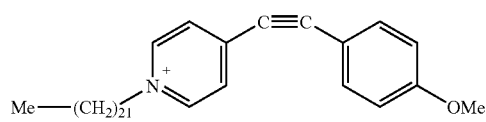

Pyridinium salt, 1-docosyl-4-[(4-methoxyphenyl)ethynyl]-

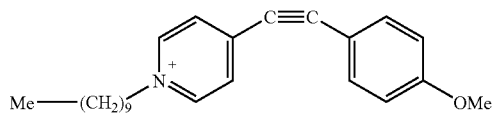

Pyridinium salt, 1-decyl-4-[(4-methoxyphenyl)ethynyl]-

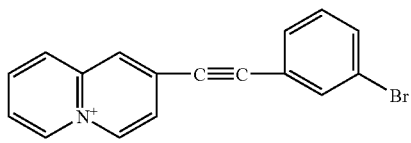

Quinolizinium salt, 2-[(3-bromophenyl)ethynyl]-

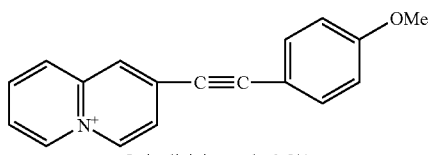

Quinolizinium salt, 2-[(4-methoxyphenyl)ethynyl]]

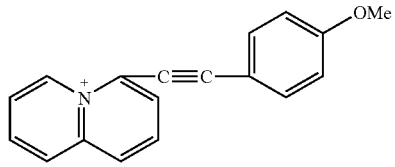

Quinolizinium salt, 4-[(4-methoxyphenyl)ethynyl]-

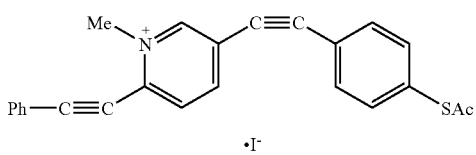

Pyridinium iodide, 5-[[4-(acetylthio)phenyl]ethynyl]-1-methyl-2-(phenylethynyl)

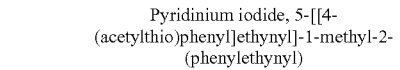
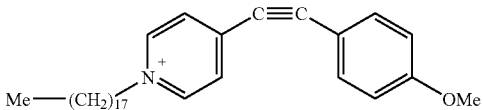

Pyridinium salt, 4-[(4-methoxyphenyl)ethynyl]-1-octadecyl-

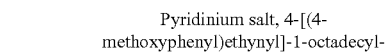
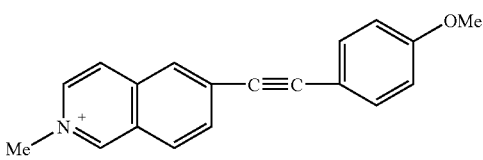

Isoquinolinium salt, 6-[(4-methoxyphenyl)ethynyl]-2-methyl

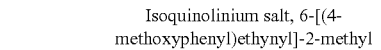
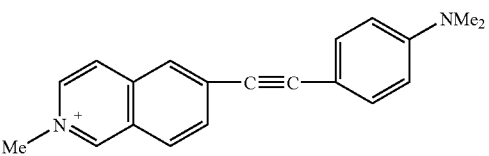

Isoquinolinium salt, 6-[[4-(dimethylamino)phenyl]ethynyl]-2-methyl

-continued

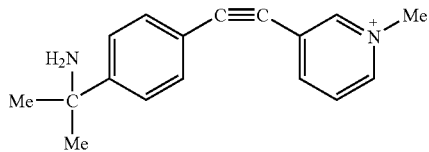

Pyridinium salt, 3-[[4-(1-amino-1-methylethyl)phenyl]ethynyl]-1-methyl

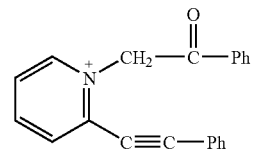

Pyridinium salt, 1-(2-oxo-2-phenylethyl)-2-(phenylethynyl)-

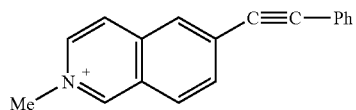

Isoquinolinium salt, 2-methyl-6-(phenylethynyl)-

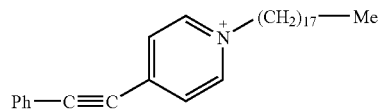

Pyridinium salt, 1-octadecyl-4-(phenylethynyl)-

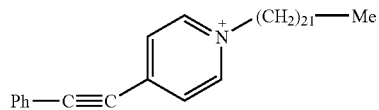

Pyridinium salt, 1-docosyl-4-(phenylethynyl)-

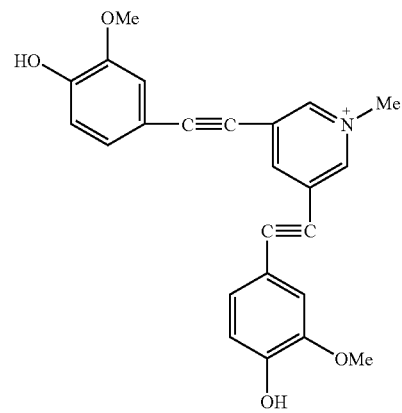

Salt of trifluoromethanesulfonic acid (1:1) and of pyridinium, 3,5-bis[(4-hydroxy-3-methoxyphenyl)ethynyl]-1-methyl

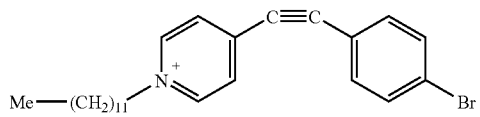

Pyridinium salt, 4-[(4-bromophenyl)ethynyl]-1-dodecyl

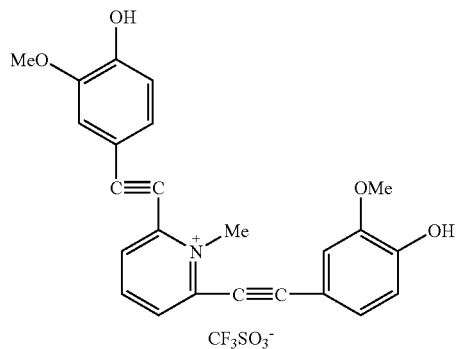

Salt of trifluoromethanesulfonic acid (1:1) and of pyridinium, 2,6-bis[(4-hydroxy-3-methoxyphenyl)ethynyl]-1-methyl -continued

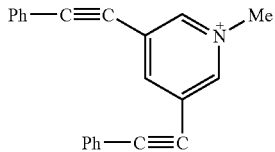

Pyridinium salt, 1-methyl-3,5-bis(phenylethynyl)-

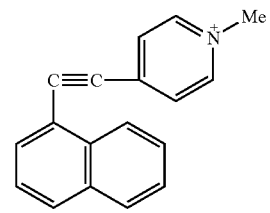

Pyridinium salt, 1-methyl-4-(1-naphthalenylethynyl)

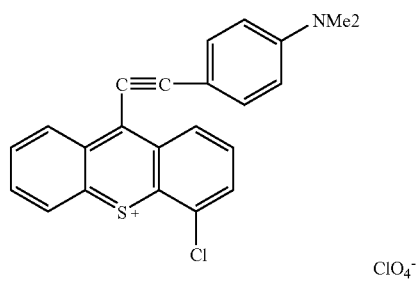

Thioxanthylium perchlorate, 4-chloro-9-[[4-(dimethylamino)phenyl]ethynyl]

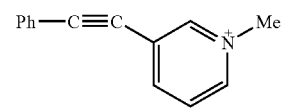

Pyridinium salt, 1-methyl-3-(phenylethynyl)-

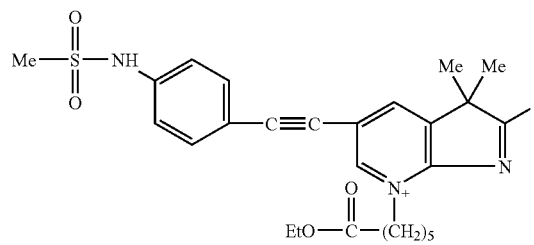

3H-Pyrrolo[2,3-b]pyridinium salt, 7-(6-ethoxy-6-oxohexyl)-2,3,3-trimethyl-5-[[4-[(methylsulfonyl)amino]-phenyl]ethynyl

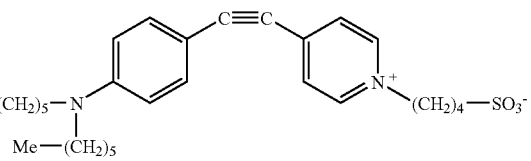

Pyridinium inner salt, 4-[[4-(dihexylamino)phenyl]ethynyl]-1-(4-sulfobutyl)

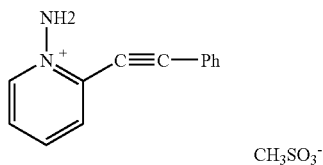

Pyridinium methanesulfonate, 1-amino-2-(phenylethynyl)

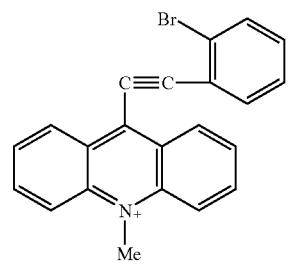

Acridinium salt, 9-[(2-bromophenyl)ethynyl]-10-methyl

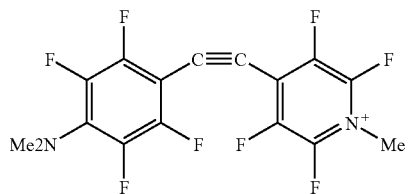

Pyridinium salt, 4-[[4-(dimethylamino)-2,3,5,6-tetrafluorophenyl]ethynyl]-2,3,5,6-tetrafluoro-1-methyl

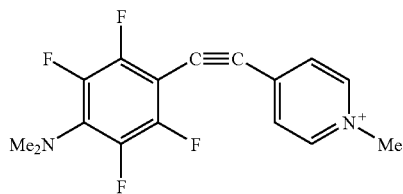

Pyridinium salt, 4-[[4-(dimethylamino)-2,3,5,6-tetrafluorophenyl]ethynyl]-1-methyl-

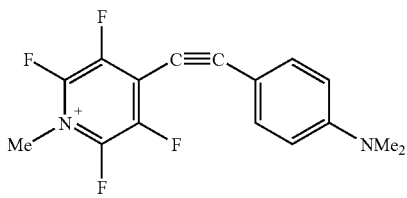

Pyridinium salt, 4-[[4-(dimethylamino)phenyl]ethynyl]-2,3,5,6-tetrafluoro-1-methyl-

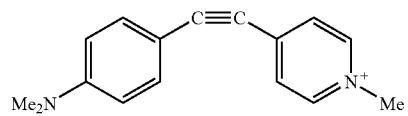

Pyridinium salt, 4-[[4-(dimethylamino)phenyl]ethynyl]-1-methyl

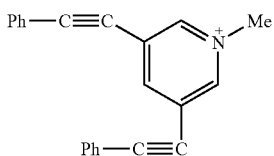

•I⁻

Pyridinium iodide, 1-methyl-3,5-bis(phenylethynyl)

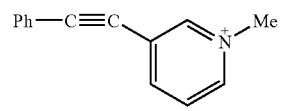

•I⁻

Pyridinium iodide, 1-methyl-3-(phenylethynyl)

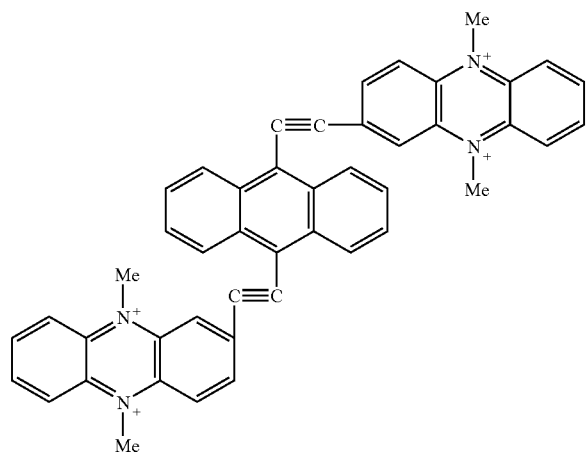

Phenazinium salt, 2,2'-(9,10-anthracenediyldi-2,1-ethynediyl)bis[5,10-dimethyl

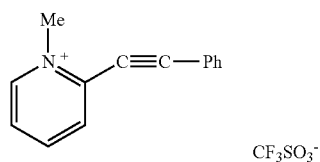

CF₃SO₃⁻

Salt of trifluoromethanesulfonic acid and of pyridinium, 1-methyl-2-(phenylethynyl)

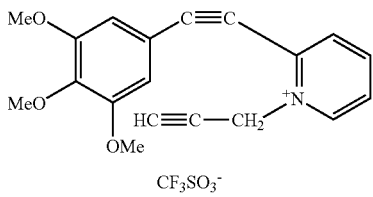

CF₃SO₃⁻

Salt of trifluoromethanesulfonic acid (1:1) and of pyridinium, 1-(2-propynyl)-2-[(3,4,5-trimethoxyphenyl)ethynyl]

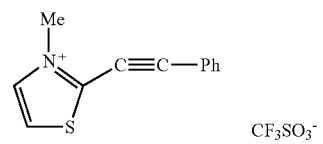

CF₃SO₃⁻

Salt of trifluoromethanesulfonic acid (1:1) and of thiazolium, 3-methyl-2-(phenylethynyl)

-continued

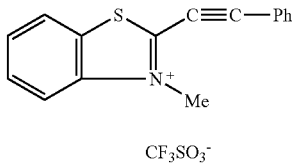

Salt of trifluoromethanesulfonic acid (1:1) and of benzothiazolium, 3-methyl-2-(phenylethynyl)

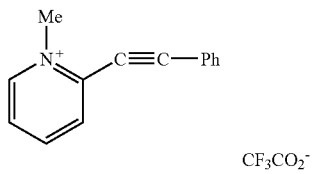

Salt of trifluoroacetic acid(1:1) and of pyridinium, 1-methyl-2-(phenylethynyl)

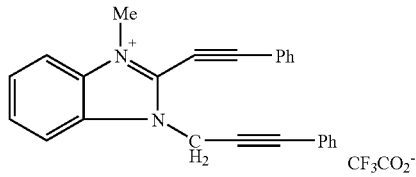

Salt of trifluoroacetic acid (1:1) and of 1H-Benzimidazolium, 1-methyl-2-(phenylethynyl)-3-(3-phenyl-2-propynyl)

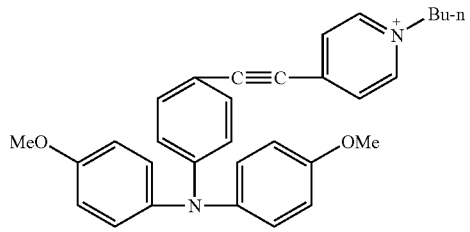

Pyridinium salt, 4-[[4-[bis(4-methoxyphenyl)amino]phenyl]ethynyl]-1-butyl

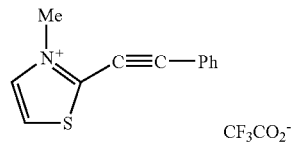

Salt of trifluoroacetic acid (:1) and of thiazolium, 3-methyl-2-(phenylethynyl)

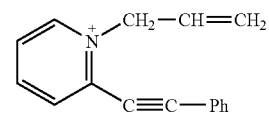

Pyridinium salt, 2-(phenylethynyl)-1-(2-propenyl)-

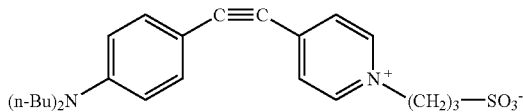

Pyridinium inner salt, 4-[[4-(dibutylamino)phenyl]ethynyl]-1-(3-sulfopropyl)

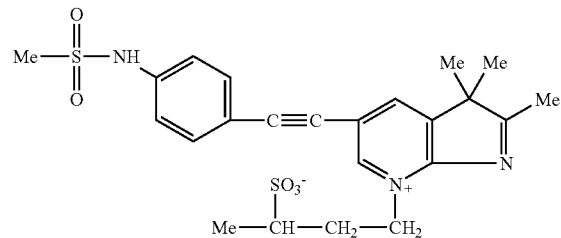

3H-Pyrrolo[2,3-b]pyridinium inner salt, 2,3,3-trimethyl-5-[[4-[(methylsulfonyl)amino]phenyl]ethynyl]-7-(3-sulfobutyl)

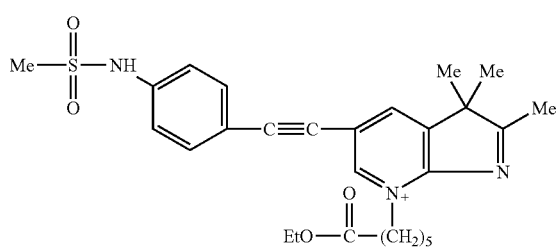

3H-Pyrrolo[2,3-b]pyridinium, 7-(6-ethoxy-6-oxohexyl)-2,3,3-trimethyl-5-[[4-[(methylsulfonyl)amino]phenyl]ethynyl]-bromide

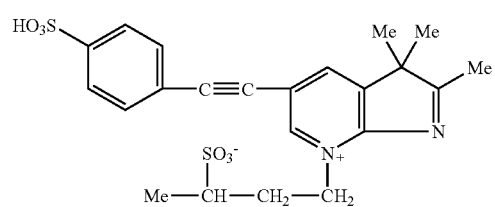

3H-Pyrrolo[2,3-b]pyridinium inner salt, 2,3,3-trimethyl-7-(3-sulfobutyl)-5-[(4-sulfophenyl)ethynyl]

-continued

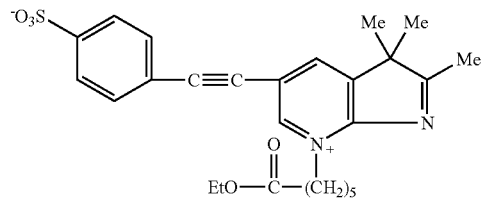

3H-Pyrrolo[2,3-b]pyridinium inner salt,
7-(6-ethoxy-6-oxohexyl)-2,3,3-
trimethyl-5-[(4-sulfophenyl)ethynyl]

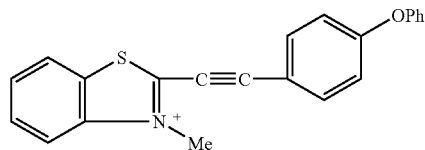

Benzothiazolium salt, 3-methyl-2-[(4-
phenoxyphenyl)ethynyl]-

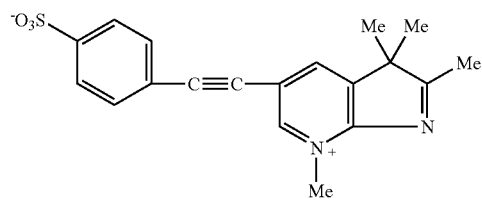

3H-Pyrrolo[2,3-b]pyridinium inner salt,
2,3,3,7-tetramethyl-5-[(4-
sulfophenyl)ethynyl]

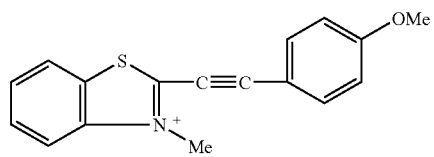

Benzothiazolium salt, 2-[(4-
methoxyphenyl)ethynyl]-3-methyl

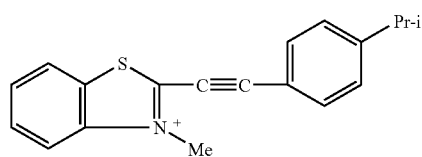

Benzothiazolium salt, 3-methyl-2-[[4-
(1-methylethyl)phenyl]ethynyl]-

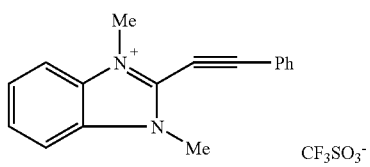

Salt of trifluoromethanesulfonic acid
(1:1) and of
1H-Benzimidazolium, 1,3-dimethyl-2-
(phenylethynyl)

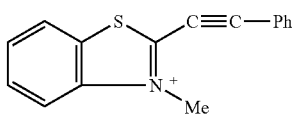

Benzothiazolium salt, 3-methyl-2-
(phenylethynyl)-

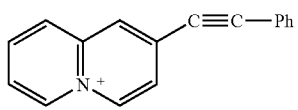

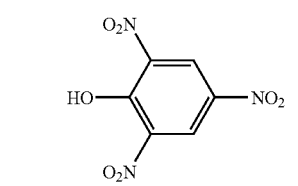

Salt of 2,4,6-trinitrophenol (1:1) and of
quinolizinium, 2-(phenylethynyl)

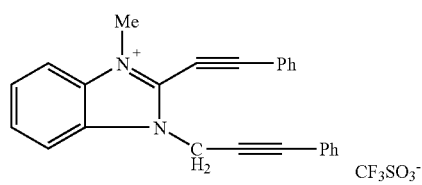

Salt of trifluoromethanesulfonic acid
(1:1) 1H-Benzimidazolium, 1-methyl-2-
(phenylethynyl)-3-(3-phenyl-2-
propynyl)

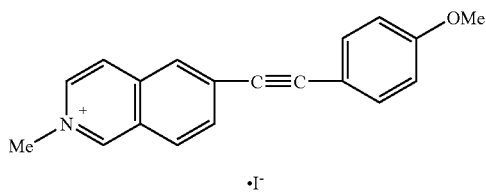

Isoquinolinium iodide, 6-[(4-
methoxyphenyl)ethynyl]-2-methyl

-continued

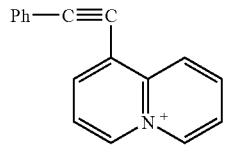

Salt of 2,4,6-trinitrophenol (1:1) and of quinolizinium, 1-(phenylethynyl)

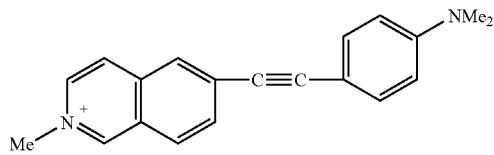

Isoquinolinium iodide, 6-[[4-(dimethylamino)phenyl]ethynyl]-2-methyl

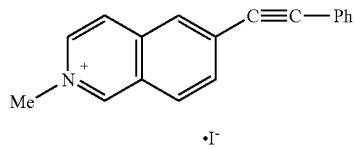

Isoquinolinium iodide, 2-methyl-6-(phenylethynyl)

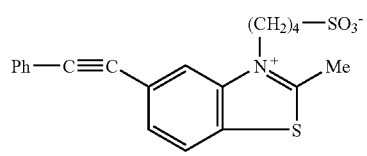

Benzothiazolium inner salt, 2-methyl-5-(phenylethynyl)-3-(4-sulfobutyl)

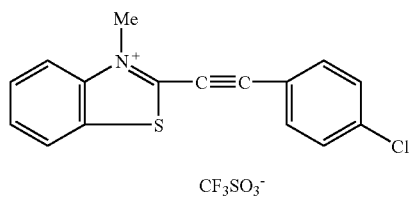

Salt of trifluoromethanesulfonic acid (1:1) and of b Benzothiazolium, 2-[(4-chlorophenyl)ethynyl]-3-methyl-,

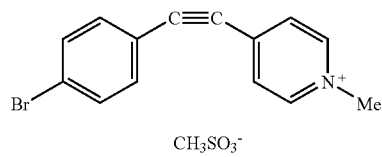

Pyridinium methyl sulfate, 4-[(4-bromophenyl)ethynyl]-1-methyl-

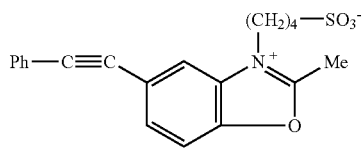

Benzoxazolium inner salt, 2-methyl-5-(phenylethynyl)-3-(4-sulfobutyl)

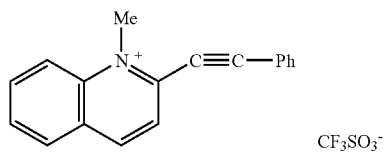

Salt of trifluoromethanesulfonic acid (1:1) and of quinolinium, 1-methyl-2-(phenylethynyl)

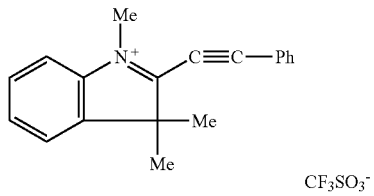

Salt of trifluoromethanesulfonic acid (1:1) and of 3H-Indolium, 1,3,3-trimethyl-2-(phenylethynyl)

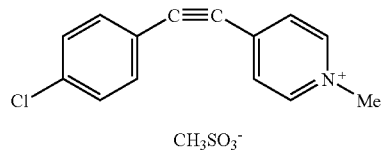

Pyridinium methyl sulfate, 4-[(4-chlorophenyl)ethynyl]-1-methyl-, methyl sulfate

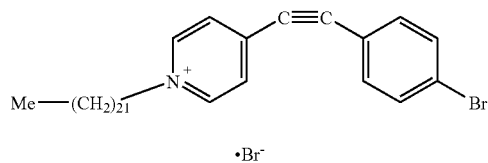

Pyridinium bromide, 4-[(4-bromophenyl)ethynyl]-1-docosyl

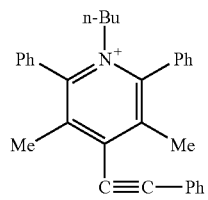

Pyridinium perchlorate, 1-butyl-3,5-dimethyl-2,6-diphenyl-4-(phenylethynyl)

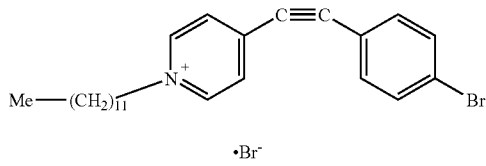

Pyridinium bromide, 4-[(4-bromophenyl)ethynl]-1-dodecyl

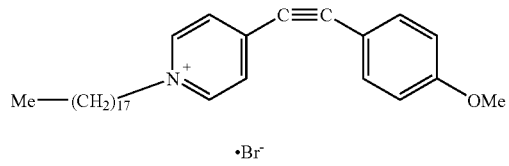

Pyridinium bromide, 4-[(4-methoxyphenyl)ethynyl]-1-octadecyl

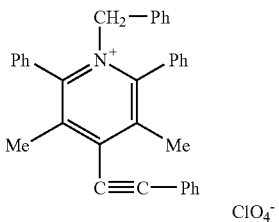

Pyridinium perchlorate, 3,5-dimethyl-2,6-diphenyl-4-(phenylethynyl)-1-(phenylmethyl)

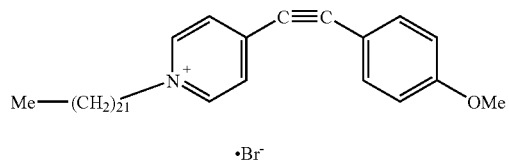

Pyridinium bromide, 1-docosyl-4-[(4-methoxyphenyl)ethynyl]

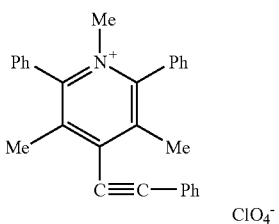

Pyridinium perchlorate, 1,3,5-trimethyl-2,6-diphenyl-4-(phenylethynyl)

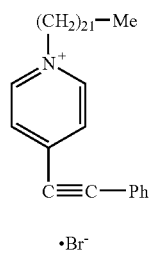

Pyridinium bromide, 1-docosyl-4-(phenylethynyl)

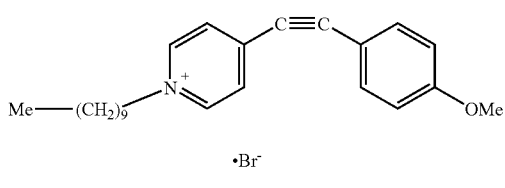

Pyridinium bromide, 1-decyl-4-[(4-methoxyphenyl)ethynyl]

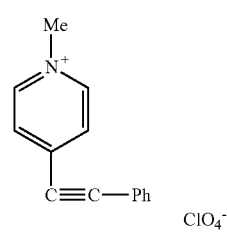

1-Methyl-4-phenylethynylpyridinium perchlorate

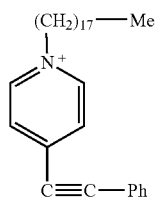

Pyridinium bromide, 1-octadecyl-4-(phenylethynyl)

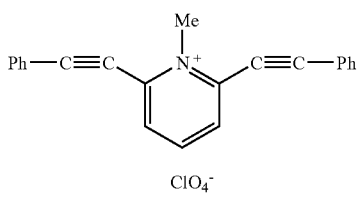

1-Methyl-2,6-bis(phenylethynyl)pyridinium perchlorate

-continued

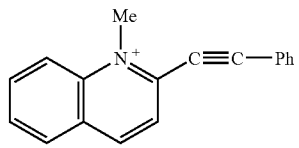

1-Methyl-2-phenylethynylquinolinium
para-toluenesulfonate

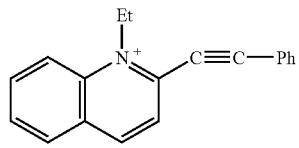

1-Ethyl-2-phenylethynylquinolinium
perchlorate

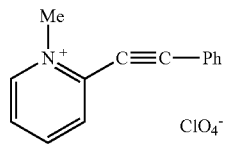

1-Methyl-2-phenylethynylpyridinium
perchlorate

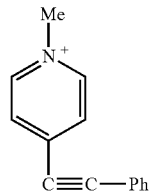

Salt of 1-Methyl-4-
phenylethynylpyridinium methyl

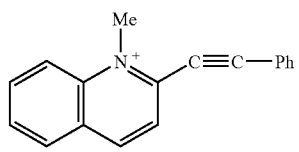

1-Methyl-2-phenylethynylquinolinium
perchlorate

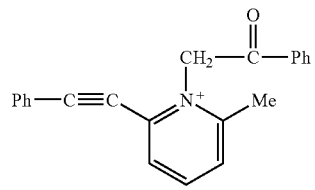

Pyridinium bromide, 2-methyl-1-(2-oxo-
2-phenylethyl)-6-(phenylethynyl)

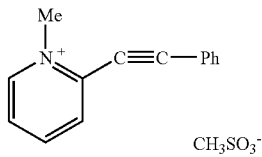

Methyl-2-phenylethynylpyridinium
methyl sulfate

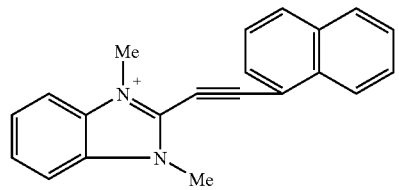

1H-Benzimidazolium 1,3-dimethyl-2-(1-
naphthalenylethynyl) methyl sulfate

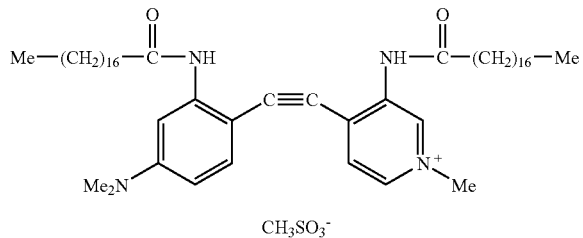

Pyridinium methyl sulfate, 4-[[4-
(dimethylamino)-2-[(1-
oxooctadecyl)amino]phenyl]ethynyl]-
1-methyl-3-[(1-oxooctadecyl)amino]

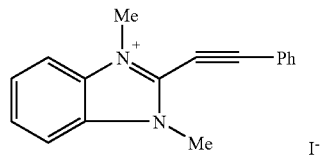

Benzimidazolium iodide, 1,3-dimethyl-2-
(phenylethynyl)-,

-continued

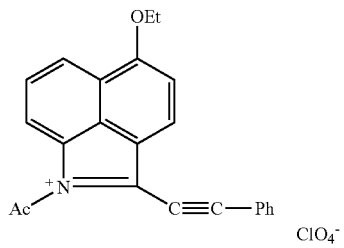

Benz[cd]indolium perchlorate, 1-acetyl-
5-ethoxy-2-(phenylethynyl)

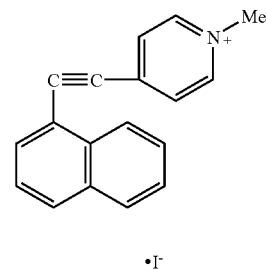

Pyridinium iodide, 1-methyl-4-(1-
naphthalenylethynyl)-,

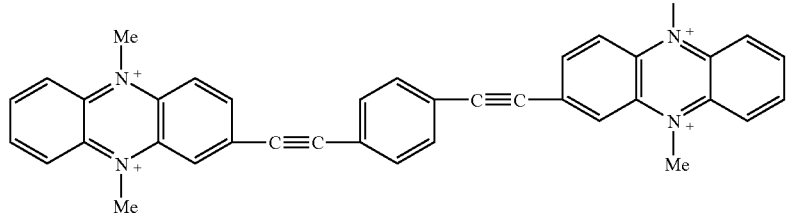

Phenazinium salt, 2,2'-(1,4-phenylenedi-2,1-ethynediyl)bis[5,10-dimethyland wherein the composition also comprises at least one surfactant present in an amount ranging from 0.01% to 50% by weight relative to the total weight of the composition, and chosen from anionic, amphoteric, nonionic, zwitterionic and cationic surfactants.

11. The composition according to claim 1, wherein the at least one direct dye is present in an amount ranging from 0.01% to 20% by weight relative to the total weight of the composition.

12. The composition according to claim 1, further comprising at least one oxidizing agent.

13. A process for treating keratin fibers, comprising:
applying to the keratin fibers a cosmetic composition comprising, in a cosmetically acceptable medium, at least one direct dye chosen from direct dyes of formulae (I), (II) and (III):

  (I)

  (II)

  (III)

wherein:
$A_1$, $A_2$ and $A_3$, independently of each other, are chosen from cationic heterocyclic groups comprising at least one quaternized nitrogen and optionally fused with at least one aromatic nucleus, and wherein $A_1$, $A_2$ and $A_3$ are attached to the at least one C≡C functional group via one of the carbon atoms of the cationic heterocycle or via the at least one aromatic nucleus to which the cationic heterocycle is optionally fused; and wherein said at least one quaternized nitrogen atom optionally bears at least one radical chosen from amino radicals; $C_2$-$C_{20}$ acyl radicals; and $C_1$-$C_{25}$ alkyl radicals optionally substituted with at least one radical chosen from phenyl, phenyl-carbonyl, ($C_1$-$C_4$)alkoxycarbonyl, sulfo (—$SO_3M$, wherein M is chosen from a hydrogen atom and alkali metals), ethylenyl (—CH=$CH_2$), acetylenyl (—C≡CH), and phenyl-acetylenyl (—C≡C—$C_6H_5$);

$A_1$, $A_2$ and $A_3$ may be optionally substituted, beyond the radicals borne by the quaternized nitrogen atoms, with at least one radical chosen from halogen atoms, $C_1$-$C_{25}$ alkyl radicals, ($C_1$-$C_4$) alkoxy radicals, ($C_1$-$C_{20}$)alkylcarbonylamino radicals, and phenyl radicals;

$B_1$, $B_2$ and $B_3$, independently of each other, are aromatic nucleuses chosen from phenyl groups, anthracenyl groups, and naphthyl groups, attached to one or two C≡C functional groups;

$B_1$, $B_2$ and $B_3$ may be optionally substituted with at least one group chosen from:
amino groups optionally bearing one or two radicals, independently of each other, chosen from $C_1$-$C_{18}$ alkyl, ($C_1$-$C_{20}$)alkylcarbonyl, ($C_1$-$C_{20}$)alkylsulfonyl, and phenyl optionally substituted with a $C_1$-$C_4$ alkoxy group;
hydroxyl;
$C_1$-$C_4$ alkoxy;
$C_1$-$C_{10}$ alkyl optionally bearing an amino group;
phenoxy;
sulfo (—$SO_3M$, wherein M is chosen from a hydrogen atom and alkali metals);
cyano;
trifluoromethyl;
halogen chosen from chlorine, fluorine and bromine; and
acetylthio ($CH_3$—CO—S—);

n is equal to 1 or 2;
the electrical neutrality of the at least one direct dye being optionally assured via at least one cosmetically acceptable anion.

14. The process according to claim 13, wherein the keratin fibers are chosen from human keratin fibers.

15. A multi-compartment device for dyeing and lightening the hair, comprising:

at least one first compartment containing a composition comprising, in a cosmetically acceptable medium, at least one direct dye chosen from direct dyes of formulae (I), (II) and (III):

  (I)

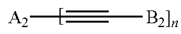  (II)

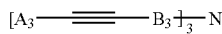  (III)

wherein:

$A_1$, $A_2$ and $A_3$, independently of each other, are chosen from cationic heterocyclic groups comprising at least one quaternized nitrogen and optionally fused with at least one aromatic nucleus, and wherein $A_1$, $A_2$ and $A_3$ are attached to the at least one C≡C functional group via one of the carbon atoms of the cationic heterocycle or via the at least one aromatic nucleus to which the cationic heterocycle is optionally fused; and wherein said at least one quaternized nitrogen atom optionally bears at least one radical chosen from amino radicals; $C_2$-$C_{20}$ acyl radicals; and $C_1$-$C_{25}$ alkyl radicals optionally substituted with at least one radical chosen from phenyl, phenyl-carbonyl, ($C_1$-$C_4$)alkoxycarbonyl, sulfo (—SO$_3$M, wherein M is chosen from a hydrogen atom and alkali metals), ethylenyl (—CH═CH$_2$), acetylenyl (—C≡CH), and phenyl-acetylenyl (—C≡C—C$_6$H$_5$);

$A_1$, $A_2$ and $A_3$ may be optionally substituted, beyond the radicals borne by the quaternized nitrogen atoms, with at least one radical chosen from halogen atoms, $C_1$-$C_{25}$ alkyl radicals, ($C_1$-$C_4$) alkoxy radicals, ($C_1$-$C_{20}$)alkyl-carbonylamino radicals, and phenyl radicals;

$B_1$, $B_2$ and $B_3$, independently of each other, are aromatic nucleuses chosen from phenyl groups, anthracenyl groups, and naphthyl groups, attached to one or two C≡C functional groups;

$B_1$, $B_2$ and $B_3$ may be optionally substituted with at least one group chosen from:

amino groups optionally bearing one or two radicals, independently of each other, chosen from $C_1$-$C_{18}$ alkyl, ($C_1$-$C_{20}$)alkylcarbonyl, ($C_1$-$C_{20}$)alkylsulfonyl, and phenyl optionally substituted with a $C_1$-$C_4$ alkoxy group;

hydroxyl;

$C_1$-$C_4$ alkoxy;

$C_1$-$C_{10}$ alkyl optionally bearing an amino group;

phenoxy;

sulfo (—SO$_3$M, wherein M is chosen from a hydrogen atom and alkali metals);

cyano;

trifluoromethyl;

halogen chosen from chlorine, fluorine and bromine; and acetylthio (CH$_3$—CO—S—);

n is equal to 1 or 2;

the electrical neutrality of the at least one direct dye being optionally assured via at least one cosmetically acceptable anion; and at least one second compartment containing a composition comprising at least one oxidizing agent.

* * * * *

UNITED STATES PATENT AND TRADEMARK OFFICE
CERTIFICATE OF CORRECTION

PATENT NO.       : 7,611,546 B2                                                      Page 1 of 1
APPLICATION NO. : 12/081310
DATED            : November 3, 2009
INVENTOR(S)      : Alain Lagrange It is certified that error appears in the above-identified patent and that said Letters Patent is hereby corrected as shown below:

On the title page, item (57), last line after "1 or 2." insert --The invention also relates to a process for treating keratin fibers, in particular human keratin fibers, using the above mentioned composition, and also to a multi-compartment device comprising it.--.

In claim 6, column 34, line 40, "is of chosen" should read --is chosen--.

In claim 8, column 34, line 47, "according claim" should read --according to claim--.

In claim 8, column 34, line 48, "is of chosen" should read --is chosen--.

Signed and Sealed this

Fifth Day of January, 2010

David J. Kappos
*Director of the United States Patent and Trademark Office*